(12) United States Patent
Ken

(10) Patent No.: US 8,172,871 B2
(45) Date of Patent: *May 8, 2012

(54) CLOSURE MEDICAL DEVICE

(76) Inventor: Christopher G. M. Ken, San Mateo, CA (US)

( * ) Notice: Subject to any disclaimer, the term of this patent is extended or adjusted under 35 U.S.C. 154(b) by 684 days.

This patent is subject to a terminal disclaimer.

(21) Appl. No.: 11/849,244

(22) Filed: Aug. 31, 2007

(65) Prior Publication Data

US 2009/0062850 A1    Mar. 5, 2009

(51) Int. Cl.
*A61B 17/08* (2006.01)
(52) U.S. Cl. .................................. 606/213
(58) Field of Classification Search .............. 606/213, 606/215, 231–233, 151, 153–154; 128/898; 623/23.72
See application file for complete search history.

(56) References Cited

U.S. PATENT DOCUMENTS

| | | | | |
|---|---|---|---|---|
| 4,730,615 A * | 3/1988 | Sutherland et al. | ........... | 606/215 |
| 4,873,976 A * | 10/1989 | Schreiber | ............... | 606/213 |
| 5,334,217 A * | 8/1994 | Das | ............... | 606/213 |
| 5,366,480 A * | 11/1994 | Corriveau et al. | ........... | 606/233 |
| 5,374,268 A * | 12/1994 | Sander | ............... | 606/148 |
| 5,527,341 A * | 6/1996 | Gogolewski et al. | ......... | 606/232 |
| 5,545,178 A * | 8/1996 | Kensey et al. | ............... | 606/213 |
| 5,649,959 A * | 7/1997 | Hannam et al. | ............... | 606/213 |
| 5,662,681 A * | 9/1997 | Nash et al. | ............... | 606/219 |
| 5,902,312 A * | 5/1999 | Frater et al. | ............... | 606/148 |
| 6,030,410 A * | 2/2000 | Zurbrugg | ............... | 606/219 |
| 6,039,753 A * | 3/2000 | Meislin | ............... | 606/213 |
| 6,387,113 B1 * | 5/2002 | Hawkins et al. | ............... | 606/219 |
| 6,406,479 B1 * | 6/2002 | Justin et al. | ............... | 606/104 |
| 6,544,267 B1 * | 4/2003 | Cole et al. | ............... | 606/74 |
| 6,551,343 B1 * | 4/2003 | Tormala et al. | ............... | 606/213 |
| 7,250,057 B2 * | 7/2007 | Forsberg | ............... | 606/213 |
| 7,335,220 B2 * | 2/2008 | Khosravi et al. | ............... | 606/213 |
| 2001/0010005 A1 * | 7/2001 | Kammerer et al. | ........... | 606/151 |
| 2001/0051815 A1 * | 12/2001 | Esplin | ............... | 606/232 |
| 2002/0058966 A1 * | 5/2002 | Tormala et al. | ............... | 606/213 |
| 2002/0169477 A1 * | 11/2002 | Demopulos et al. | ......... | 606/215 |
| 2004/0225305 A1 * | 11/2004 | Ewers et al. | ............... | 606/153 |
| 2005/0085851 A1 * | 4/2005 | Fiehler et al. | ............... | 606/213 |
| 2005/0107827 A1 * | 5/2005 | Paprocki | ............... | 606/228 |
| 2005/0125031 A1 * | 6/2005 | Pipenhagen et al. | ......... | 606/213 |
| 2005/0251210 A1 * | 11/2005 | Westra et al. | ............... | 606/232 |
| 2005/0283192 A1 * | 12/2005 | Torrie et al. | ............... | 606/228 |
| 2006/0229672 A1 * | 10/2006 | Forsberg | ............... | 606/232 |
| 2006/0229673 A1 * | 10/2006 | Forsberg | ............... | 606/232 |
| 2006/0229674 A1 * | 10/2006 | Forsberg | ............... | 606/232 |
| 2006/0264975 A1 * | 11/2006 | Pipenhagen et al. | ......... | 606/144 |
| 2006/0265006 A1 * | 11/2006 | White et al. | ............... | 606/232 |
| 2006/0265007 A1 * | 11/2006 | White et al. | ............... | 606/232 |
| 2006/0280768 A1 * | 12/2006 | Hwang et al. | ............... | 424/423 |
| 2007/0032823 A1 * | 2/2007 | Tegg | ............... | 606/232 |
| 2007/0032824 A1 * | 2/2007 | Terwey | ............... | 606/232 |
| 2007/0156174 A1 * | 7/2007 | Kaiser et al. | ............... | 606/215 |
| 2007/0255314 A1 * | 11/2007 | Forsberg | ............... | 606/213 |
| 2007/0276433 A1 * | 11/2007 | Huss | ............... | 606/213 |
| 2008/0097521 A1 * | 4/2008 | Khosravi et al. | ............... | 606/213 |

* cited by examiner

Primary Examiner — Melanie Tyson
Assistant Examiner — Son Dang
(74) Attorney, Agent, or Firm — Leigh H. Firestone

(57) ABSTRACT

A closure device for closing a puncture wound has a distal section that can be placed against the interior wall of a vessel and a proximal section that bunches in the tissue tract to close the wound.

20 Claims, 12 Drawing Sheets

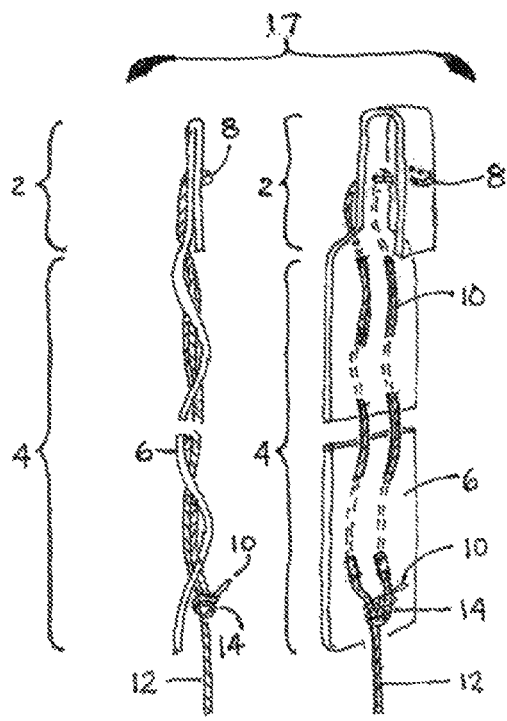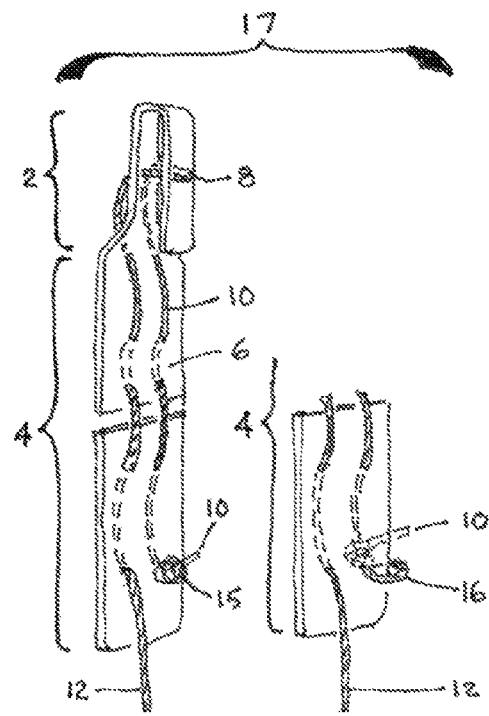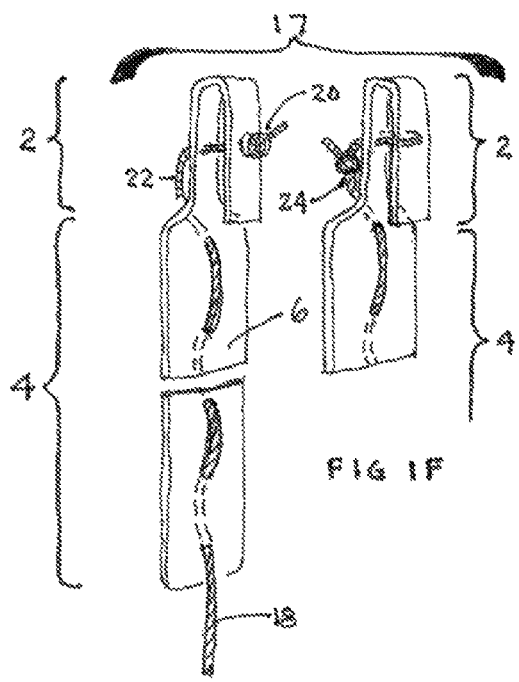

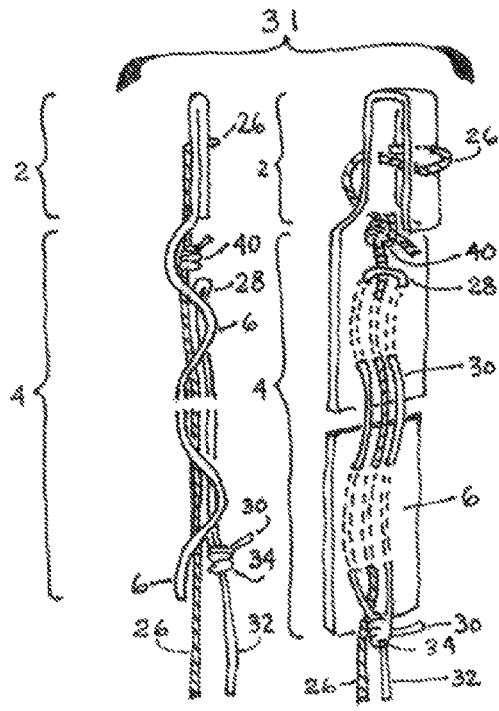
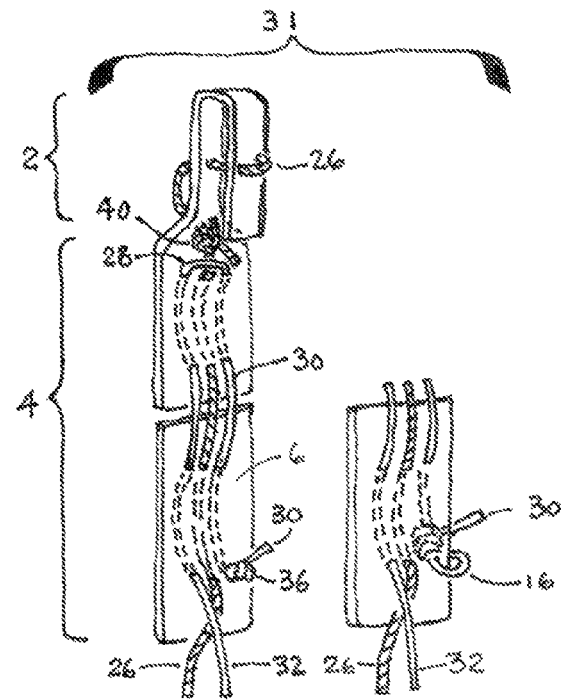
FIG 2A  FIG 2B  FIG 2C  FIG 2D
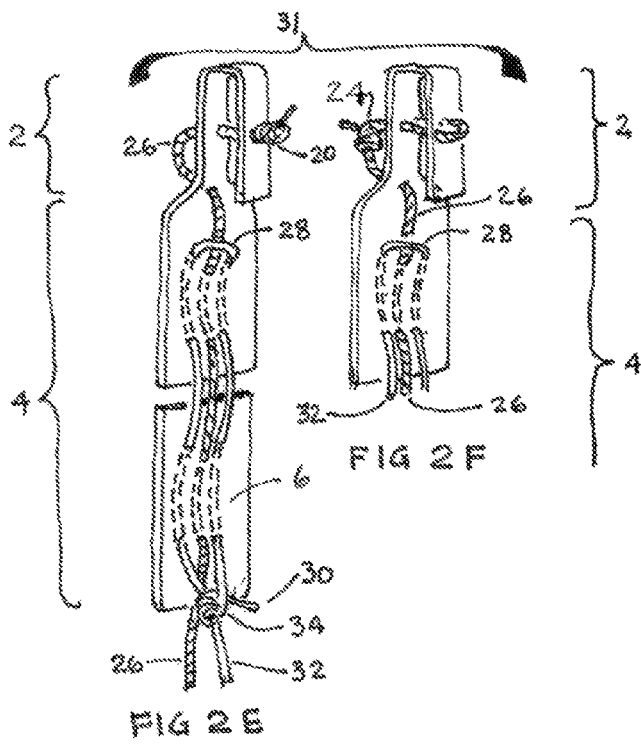
FIG 2E  FIG 2F

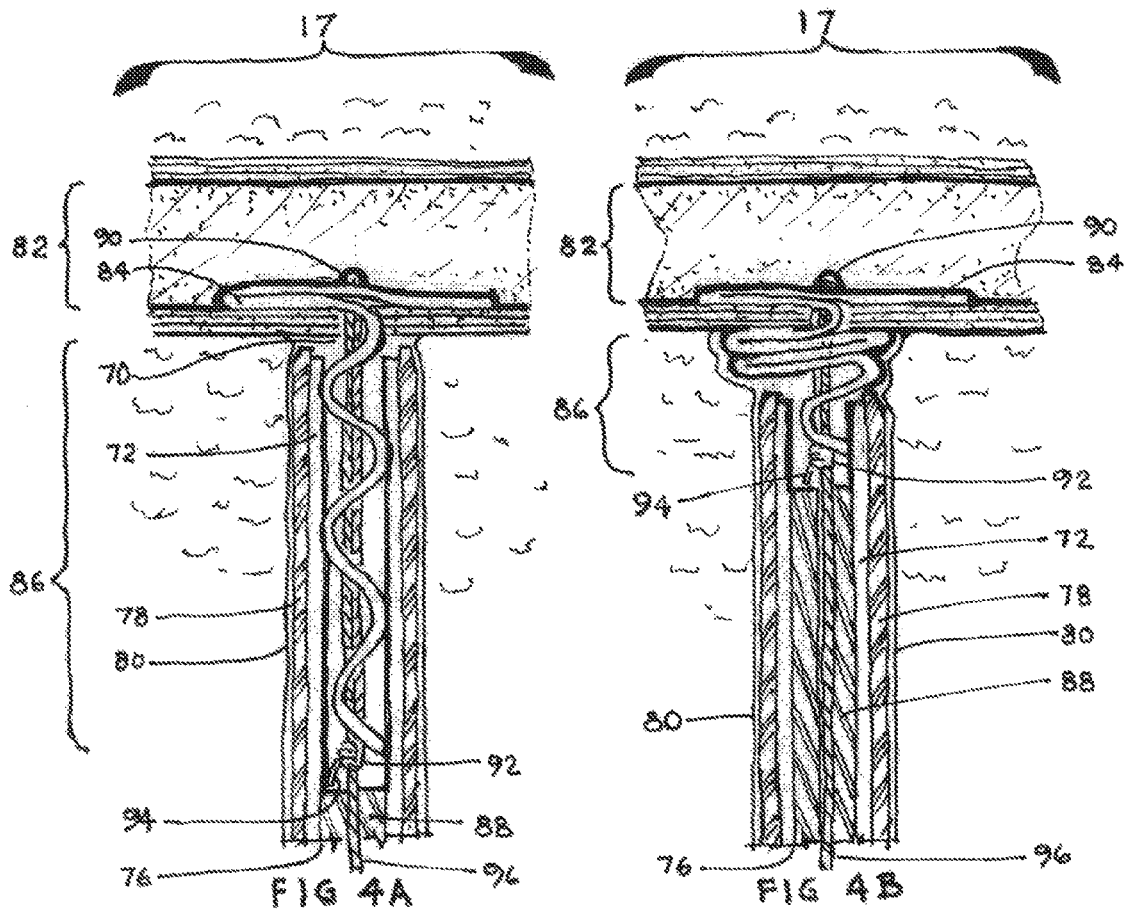
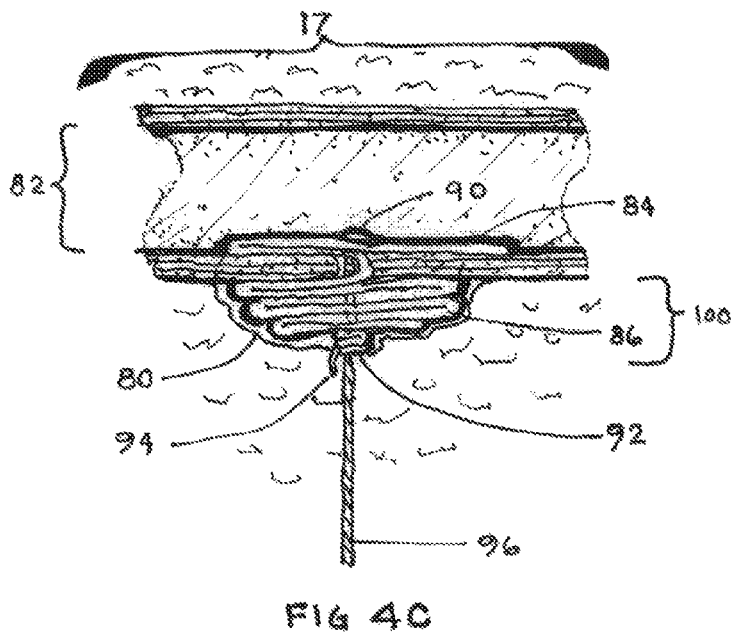

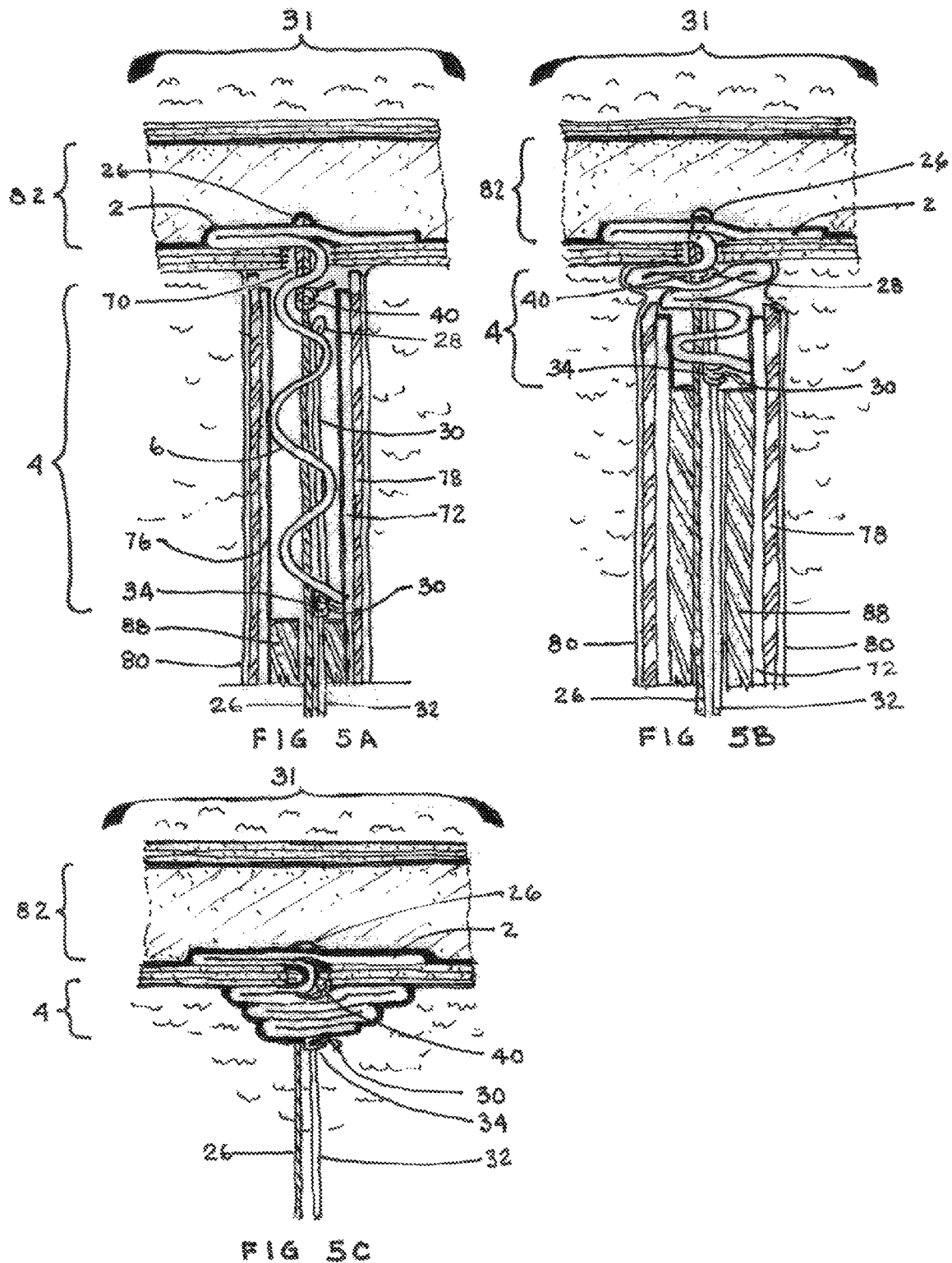

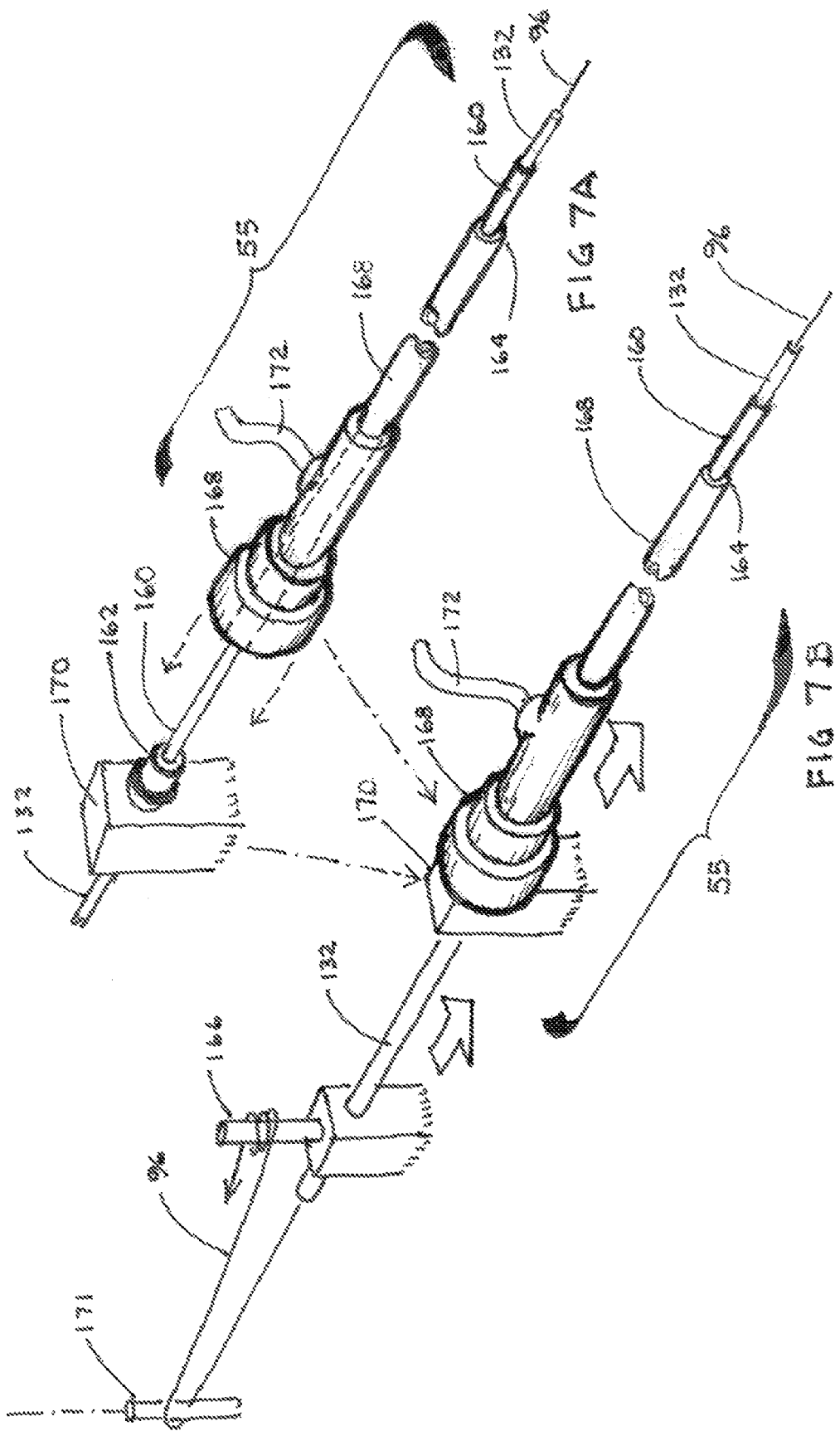

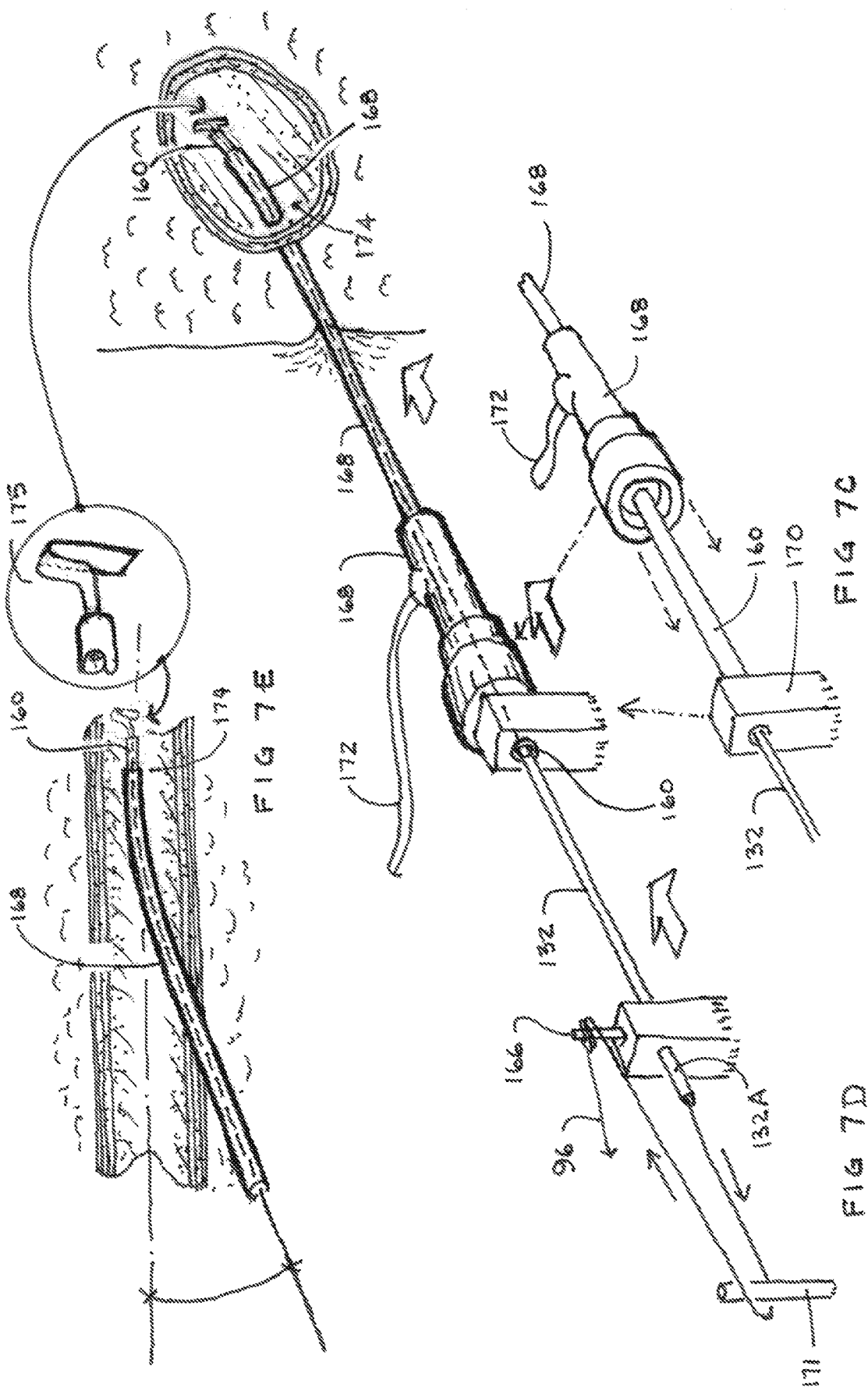

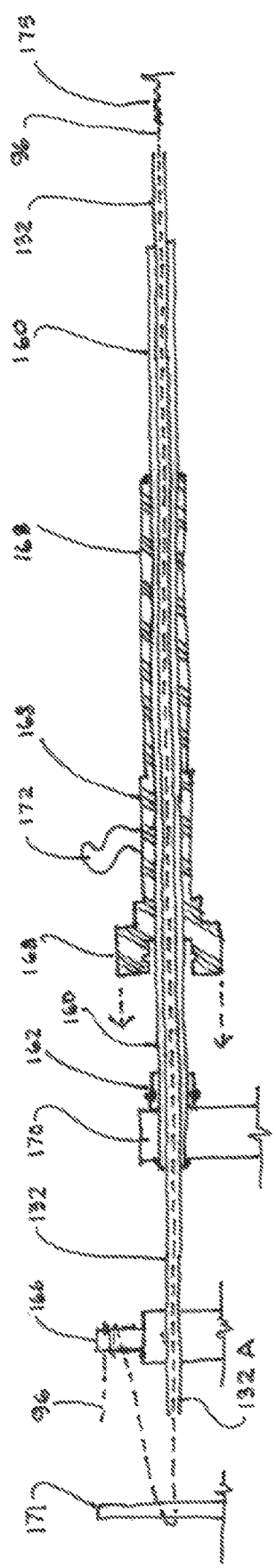

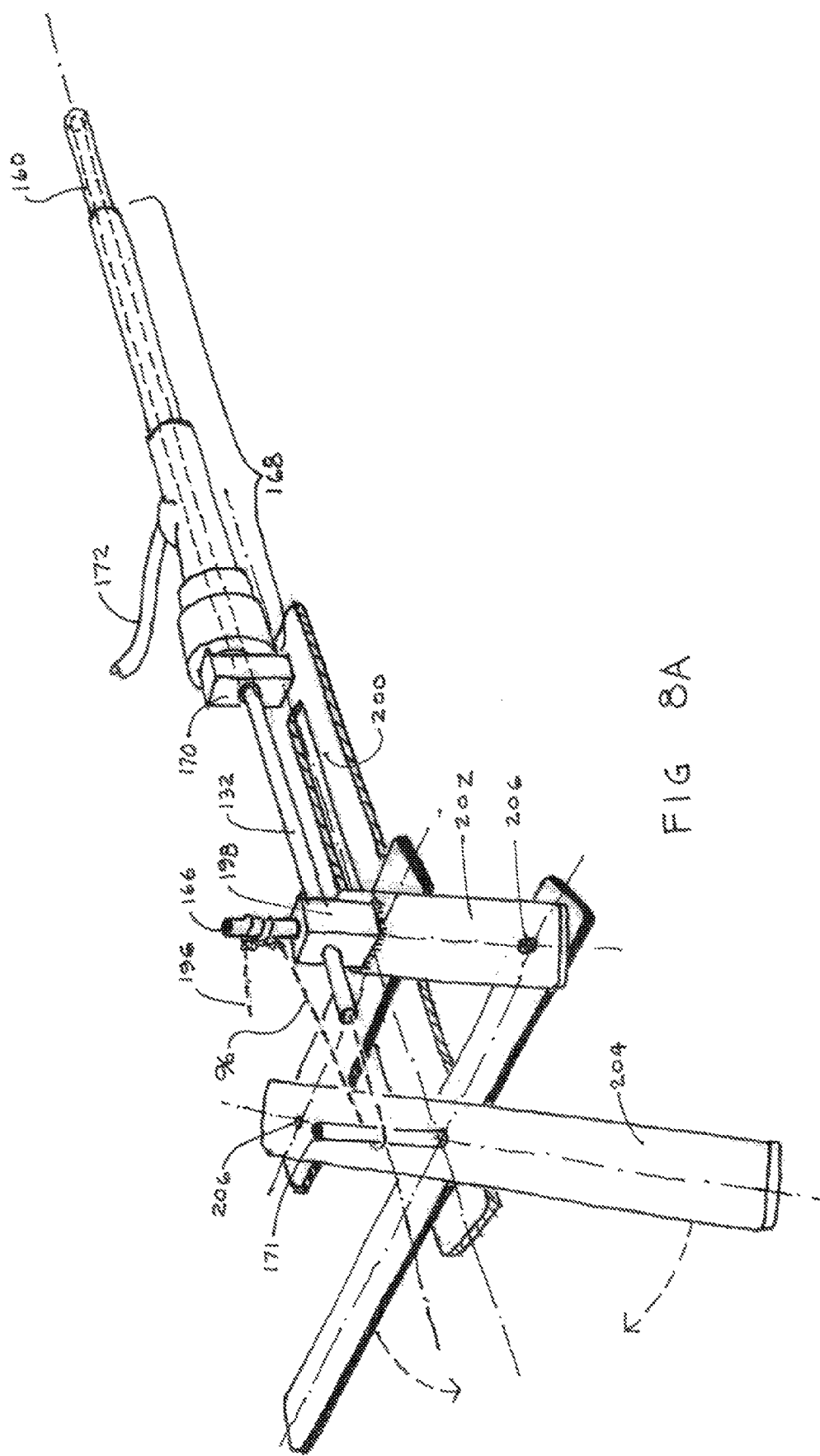

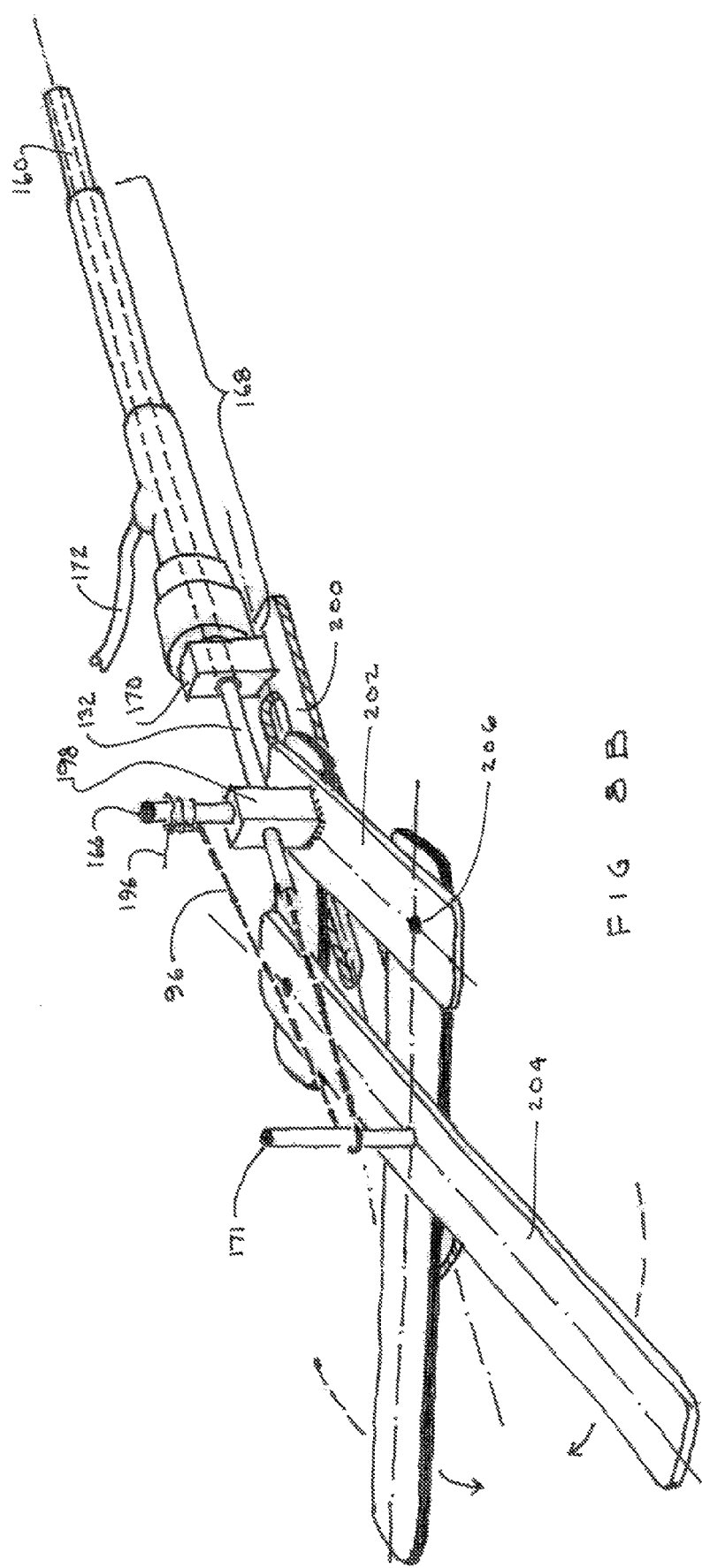

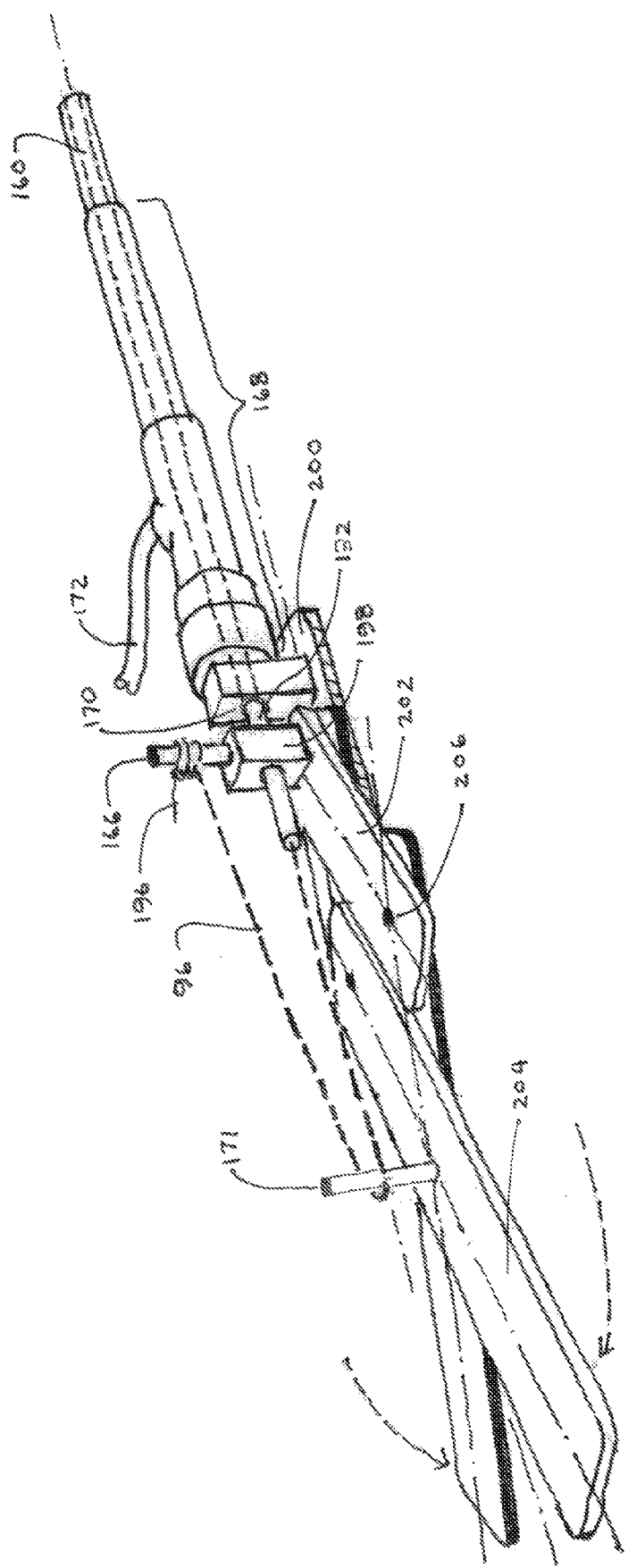

CLOSURE MEDICAL DEVICE

FIELD OF THE INVENTION

The invention is a closure device for closing a wound caused by a minimally invasive medical procedure that accesses the body through a vessel or cavity. The device and method of the invention provide for wound closure upon completion of such a minimally invasive procedure. The device is made of bunchable material that bunches in the tissue tract and provides a structural environment that stops bleeding and promotes healing of the tissue.

BACKGROUND OF THE INVENTION

Many vascular procedures can be accomplished by minimal invasion, typically by accessing the femoral artery or another major blood vessel, and through that vessel accessing the heart, brain, or other site that requires surgical attention. When the procedure is completed a hole remains in the accessed vessel that needs to be closed. The goal of repair of the puncture wound is to create hemostasis in the tissue tract, and to allow the puncture hole in the vascular lumen to seal, allowing blood to eventually re-flow through the lumen without thrombosis or embolism, and also allowing the tissue in the tissue tract leading to the vessel to heal.

The earliest methodology of closing puncture wounds in vascular lumens was direct physical pressure which is first applied by a person (usually a physician or nurse or aid) for up to an hour. After the initial application of manual pressure, a "C" clamp is fixed at the puncture site to finish the closure. Usually during application of the "C" clamp the patient is immobilized for 6 to 8 hours. The "C" clamp method can be painful and as with manual direct pressure requires immobilization. The drawbacks of direct pressure at the site include that a trained professional is monopolized with the task for a relatively long period of time, there is a risk of thrombosis or embolization during the process of applying pressure, the circulation is cut off in the lumen when the pressure is being applied, the patient is immobilized during application of the pressure, and it is painful. The pressure methods generally require also that the patient be catheterized for urinary output during the 8 or so hours while the wound is closing under pressure from the "C" clamp so that the patient can remain completely immobilized until the wound has closed sufficiently to stop any bleeding from the artery. Even today, despite the discomfort and extended care required while applying direct pressure and waiting for the wound to heal, direct pressure, either by manual application or a "C" clamp, or a combination of both, is the standard of care. About 70% or all closure requirements are met with this crude and seemingly archaic method of closure by application of direct pressure.

As an alternative to direct pressure, inventors and companies have developed various devices for wound closure at a vascular puncture site. Accordingly, on the market today are various items including: biodegradable plugs, suture, staples, ultrasound, collagen, collagen with thrombin, collagen with an anchor, and hemostatic patches and pads. These commercial alternatives to direct pressure include Kensey Nash's AngioSeal that places a member in the artery from which a second operation can be facilitated to add a plug on the outside of the artery. Abbott's Perclose system sutures the site using a remote access introducer. Also available are Datascope's VasoSeal, Vascular Solutions' Duett, Sutura's vascular suturing system, and Marine Polymer Technologies' Syvek. Of the 30% of the market that uses these devices instead of direct pressure, the devices used most often are AngioSeal (46%), PerClose (32%), VasoSeal (14%), and Duett (3%). Obese patients are among the best candidates for these alternatives because direct pressure on an obese person can be less effective than necessary for complete closure of the puncture site. Some of these methods or devices have proved unreliable, generating thrombosis, or requiring placement several times before they are effective. Although these devices are expensive, successful use of them, can reduce the overall cost of the procedure if use of the device causes the patient to be ambulatory sooner and require less attendant care and less hospital time as a result.

It would be advantageous to the field of percutaneous and otherwise minimally invasive surgery (including particularly cardiac and cardiac-related surgery) to offer a system of vascular closure that is simple and capable of providing reliable hemostasis in the accessed vessel at a cost that can justify incorporation of the device into routine practice. In addition, present practice sometimes indicates using two or more devices to accomplish the closure, and it would be optimal to provide a single effective device that reliably closes the puncture site every time. In addition, it would be desirable to accomplish closure without suture, and without the need to apply direct pressure, even as an adjunctive therapy. The present invention accomplishes these and other goals.

SUMMARY OF THE INVENTION

The invention is a device for closing a puncture wound in a mammalian body, particularly a human body. The typical situation where this device is used is after a minimally invasive procedure where the heart or related vessels are accessed through the femoral artery. After the procedure, a hole remains in the femoral artery that can bleed unless closed. The invention is a device that can be placed into the femoral artery and through the hole and within the exiting tissue tract.

A delivery sheath holding the device is placed through the introducer sheath that is already in the tissue tract and femoral artery from the minimally invasive procedure. When deployed the device closes the tissue tract and seals the puncture within the femoral artery shut so that the patient does not bleed into the tissue tract and blood can resume normal flow through the artery.

The wound to be closed can be any puncture wound, particularly wounds caused in percutaneous minimally invasive surgery where an artery such as a femoral artery is accessed using a catheter. Removal of the catheter and its introducer sheath after the procedure results in a hole leading from the vessel. Bleeding will ensue if the hole is not plugged either by thrombosis created by direct pressure or some device to close the hole. The device of the invention closes the puncture hole, and can also close a similar hole left after access to a cavity or other body vessel. The device is deliverable in a delivery sheath, and the delivery sheath is optimally passed through the introducer sheath already in place from the surgery that was the purpose of creating the puncture wound in the first place. The puncture wound typically has a length along a tissue tract that leads from the puncture in the vessel or cavity to the skin, the tissue tract resolving in an interior opening of the vessel or cavity.

The closure device will have minimally a distal section for placing inside the interior opening of the vessel or cavity. The distal section is lodged in a delivery sheath to effect delivery to the vessel along the tissue tract that was already created with the introducer sheath for the percutaneous procedure. The delivery sheath has a proximal end at the skin surface and a distal end close to the interior of the vessel or cavity where the distal section is to be delivered. The delivery sheath is capable of penetrating the wound along the length of the wound to pass through the interior opening of the vessel and release the distal section. The distal section is released using a plunger that slides over a tension member. The tension member is affixed to the distal section and tension placed on the tension member. The tension member is typically a suture or string or other type of strand or linear member able to withstand tension and it controls the placement and directionality and seating of the distal section at the vessel or cavity wall, in coordination with the action of the plunger in the delivery sheath that pushes the distal section out from the sheath while tension is placed on the distal section by pulling the tension member proximally toward the skin surface. In this manner a distal section having a stiff front end is released from the delivery sheath and rotated 90 degrees so that the stiff front end is now turned perpendicular to the opening of the delivery sheath, and is no longer parallel to it. The distal section of the device when seated in the vessel or cavity wall provides resistance against the interior opening, allowing for the placement and adjustment of the rest of the device.

The device also minimally comprises a proximal section connected to the distal section. The proximal section comprises a bunchable material capable of bunching in the tissue tract upon deployment. As the proximal section releases from the delivery sheath it is unbunched, but tension placed on the tension member, which is a string or strand running through the bunchable material, causes the material to bunch and fold in the tissue tract. The device also minimally has at least one tension member that is a string or strand connected to the distal section and either the same or a different tension member connected to the proximal section for pulling each section. Pulling on the tension member adjusts the position of the distal section, and bunches the proximal section. Positioning of the device in the body is with the distal section seated against the interior of the vessel wall, and the proximal section bunched in the tissue tract. The tension member or tension members are left to reside in the device and can be clipped at the skin level. The end or ends of a tension member at the skin surface can be used to retrieve the closure device if it was not positioned properly, or if for any reason the closure device needs to be removed or readjusted.

The configuration and placement of the tension member in the device can be important. The tension member can be a single string knotted at the distal section and threaded through the proximal section. Alternatively, the tension member can be looped through the distal section and proximal sections, effectively providing for two ends at the proximal section of the device near the skin surface. In order to pull the looped tension member effectively, the tension member can be slip knotted to itself in the proximal section so that pulling on the string resulting from the slip knot bunches the material as the slip knot travels down the device toward the distal section. This activity can be facilitated better using a plunger that pushes the device away from the skin surface and towards the vessel opening, while the tension member with its slip knot is pulled back towards the skin surface to provide the tension necessary for positioning the distal section and bunching the proximal section.

Several configurations of the tension member can be used including that the tension member is looped through the distal section and proximal section using a single tension member having first and second proximal ends (ends residing at or near the skin surface). The tension member can also pass through the distal section and the proximal section once and be knotted at said distal section, so that there is only a single end at the proximal section. A slip knot configuration of the tension member provides greater tension and control on the bunching material, and is achieved by having two ends of the same tension member (created when the tension member is threaded or looped through the material) then forming a slip knot with one of the ends around the other end so that pulling the single remaining thread of the slip knot causes the material to compress. The pulling of the tension member is usually done in coordination with the pushing of a plunger away from the skin and towards the vessel or cavity opening.

Another variation of the device includes a middle section positioned between the distal section and the proximal section. Although the middle section can be the same width as the proximal section, the middle section is optimally a narrow short section for passing from the vessel to the tissue tract. The middle section is connected to the distal section so that upon rotation of the distal section, the middle section remains exterior to the vessel or cavity, remaining in connection with the distal section. The middle section is optimally significantly narrower than the distal section (the rotated distal section) so as to provide minimal disturbance between the interior opening of the vessel or cavity and the tissue tract.

Following from the middle section in this variation is the proximal section that bunches as before. A single tension member can control all three sections, or two tension members can be used, one controlling the distal section, and another controlling the middle and proximal sections together. Also, the middle section does not necessarily need to have a tension member controlling it at all, so that two tension members can be used, one for the distal section and one for the proximal section. The second tension member can start in the middle section or can miss the middle section altogether and start in the proximal section because the middle section is so short and narrow it does not bunch much if at all, nor is it important for it to bunch, but rather the middle section acts as a placeholder or a distancer to separate the distal from the proximal sections and provide the least possible trauma at the vessel or cavity opening. The knotting of the tension members can have the same variations as described previously, ie. a single thread knotted at the distal section, a single thread knotted at the proximal section, a single thread looped through all sections with two ends at the skin surface, the two ends at the skin surface forming a slip knot, or both a single thread looped at the vessel end of the proximal section with two ends at the skin surface, preferably controlled by a slip knot there.

Yet another variation of the device includes a distal section, a middle section, a proximal section and two tension members in essentially the same configurations as described previously. The only difference in this variation is that after the proximal section has been bunched using the second tension member, the first tension member is used to pull the distal section from its seat in the interior of the vessel or cavity wall into the beginning of the tissue tract to reside adjacent to or just in front of the middle section. This variation is depicted in FIGS. 6A, 6B, and 6C.

Methods of closing a puncture wound include using each of the described variations as depicted in a procedure to close a puncture wound. Accordingly, the wound can be closed with a device having a distal and proximal section and a single tension member; a distal and proximal section and two tension members; a distal, proximal, and middle section having two tension members; and a distal, proximal and middle section having two tension members where the first tension member is capable of pulling the distal section out of the interior of the vessel or cavity for final configuration of the device entirely outside the vessel or cavity.

The tension member can also be fixed by one knot in the tension member at the distal section. The rest of the tension member is threaded through the material and pulling on the tension member while the plunger pushes against the material accomplishes the necessary activity for deploying the device. An alternative configuration for any of the tension members is a slip knot formed at or near the skin surface for better pulling on the tension member and control or bunching of the distal or proximal sections.

The distal, middle and proximal sections can comprise any suitable biocompatible material. Preferred material is material that will bioabsorb or biodegrade at about the rate that the wound will heal. Accordingly, materials that may be used to make the device include but are not limited to polyglycolytic acid (PGA), PGLA, PLA, polydioxanone, polycaprolactone, polyhydroxybutyrate, collagen, a polymer matrix, extracellular matrix, silk, Dacron, polytetrafluoroethylene (PTFE), expanded polytetrafluoroethylene (EPTFE), a metal, a metal alloy, a plastic, an elastic material, a polymer, an inert material, a fused segment of material, a melted segment of material, a fabric, a braid, a weave, and a foldable material.

Similarly, the tension members can comprise materials that have sufficient tensile strength to withstand the pulling activity, and that also, sometime when the wound has healed will itself biodegrade. Thus, the tension member can comprise a material selected from the group consisting of polyglycolytic acid (PGA), polyglycolytic lactic acide (PGLA), polylactide (PLA), polydioxanone, polycaprolactone, polyhydroxybutyrate, collagen, a polymer matrix, extracellular matrix, silk, Dacron, suture, a bioabsorbable material, a biodegradable material, a biocompatible material, a metal, a metal alloy, a plastic, an elastic material, a polymer, an inert material, a thread, and a strand.

Other variations of the device include the elements just described above, with some notable additions or differences. One variation includes a device where the distal section and the proximal section each have their own separate tension members. As with all the tension members of the variations, these tension members can be looped with a slip knot, or singly threaded through with an end knot.

The first tension member controls and seats the distal section and the second tension member bunches and positions the proximal section. The process of placing the device includes the activities of pushing the plunger distally in the delivery sheath so that the distal section is deployed, rotating the distal section about 90 degrees once inside the vessel or cavity by pulling on a tension member that controls the distal section (i.e. is attached to it), seating the distal section in its rotated state against the wall of the vessel or cavity, withdrawing the introducer sheath and delivery sheath gradually along the tissue tract while pushing with the plunger to expel the proximal section in the tissue tract, and bunching the proximal section by pulling on the tension member somewhat simultaneously as the plunger is being pushed toward the vessel or cavity opening. The methods can further include locking the delivery sheath (which resides within the introducer sheath during much of the delivery process) within the introducer sheath.

The invention also includes a mechanism for delivering the closure devices that includes a delivery sheath having distal and proximal ends, a tension member control arm at the proximal end for allowing pull on the tension member to place the distal section and bunch the proximal section. The mechanism also comprises a plunger that resides within the delivery sheath with one or more tension members running through it so that the tension members can be pulled while the plunger is pushed to effect delivery of the device.

Another variation of the device is a closure device for closing a puncture wound, the device deliverable in a delivery sheath, the puncture wound having a length along a tissue tract that resolves in an interior opening of a vessel having fluid flow, the closure device comprising a short stiff front section capable of rotation 90 degrees upon placement inside said vessel for seating the device in the vessel, the short front section having a first tension member for seating it, and the short front section connected to a long bunchable back section that bunches upon deployment from the delivery sheath using a plunger to push it out from the delivery sheath and a second tension member running through a bunchable section to pull against the seated front section in opposition to the plunging action to release the long back section from the delivery sheath and to bunch it in the tissue tract.

Yet another variation of the device provides that the device is as just described and additionally the short stiff front section bends at a midline after said long bunchable back section is bunched using the first tension member to withdraw the short stiff front section from the interior opening and bend it into the tissue tract in front of the long bunched back section, thereby clearing the vessel of the device and providing unobstructed fluid flow in the vessel.

BRIEF DESCRIPTION OF THE DRAWINGS

FIG. 1A depicts a side view of one embodiment of the device having a distal section, a proximal section, and a tension member looped through both sections with a slip knot at the proximal end.

FIG. 1B depicts a flat view of the device of FIG. 1A with the distal section, proximal section and tension member looped through both of them with a proximal slip knots.

FIG. 1C depicts another embodiment of the device with a distal section, proximal section, and tension member looped through both, the tension member ending with an end knot at one of the two proximal ends.

FIG. 1D depicts the proximal most end of the embodiment of FIG. 1C having an end loop knot instead of an end knot.

FIG. 1E depicts another embodiment of the device having a distal section, a proximal section, and a tension member through both of them, with an anchoring end knot in the distal section.

FIG. 1F depicts the distal end of the device of FIG. 1E having a looped knot for anchoring the tension member in the distal section.

FIG. 2A depicts a side view of a partially folded device having a distal section, a proximal section and two tension members, one in the distal section and passing through the proximal section also and one through just the proximal section. The embodiment of FIG. 2A depicts a slip knot at an end of the tension member in the distal section, and a slip knot at one end of the tension member that runs through the proximal section.

FIG. 2B depicts a flat view of the device of FIG. 2A showing the looped tension member through the distal section, ending in a slip knot, and the looped tension member through the proximal section, ending in a slip knot proximal to the proximal end.

FIG. 2C depicts a flat view of another embodiment having two tension members, where the proximal end of the proximal tension member is finished in an end knot.

FIG. 2D depicts a variation of the embodiment of FIG. 2C showing a looped end knot to finish the tension member that runs through the proximal section.

FIG. 2E depicts an embodiment of the device having a distal end with a tension member having an end knot at the top, the tension member extending through the proximal section also, and a second tension member in the proximal section that is looped around and has a slip knot at the end of the proximal section closest to the skin surface (the proximal end of the proximal section).

FIG. 2F is a version of the embodiment of FIG. 2E that has a looped knot at the distal section to hold the single tension member in the distal section, and is otherwise the same with respect to the second tension member.

FIGS. 4A, 4B, and 4C depicts the embodiment of FIGS. 1A and 1B in the context of a vessel and tissue tract. FIG. 4A depicts the distal section placed in the interior of the vessel and the proximal section beginning to bunch in the tissue tract. FIG. 4B depicts the proximal section folding more extensively using the plunger of the delivery device to effect the bunching along with the tension member. FIG. 4C depicts the device fully placed in the vessel and tissue tract, and the delivery device removed.

FIG. 5A depicts the embodiment of FIGS. 2A and 2B in the context of a vessel and tissue tract. FIG. 5A depicts the distal section placed in the interior of the vessel having the tension member with a slip knot, and the proximal section beginning to bunch in the tissue tract. FIG. 5B depicts the proximal section almost completely bunched having the plunger of the delivery device pushed distally to bunch the proximal section along with pulling on the second tension member having a slip knot. FIG. 5C depicts the device completely placed in the vessel and tissue tract and the delivery device removed.

FIG. 6A depicts the distal section placed in the interior of the vessel and the proximal section beginning to bunch in the tissue tract. FIG. 6B depicts the middle section bunching slightly, and the proximal section bunching completely in the tissue tract using the plunger of the delivery device and the second tension member having a slip knot. FIG. 6C depicts the middle section bunching and the proximal section completely bunched in the tissue tract, and the distal section beginning to bend in half. FIG. 6D depicts the device with the distal section completely withdrawn from the interior of the vessel to reside bunched with the middle section in the early part of the tissue tract, and following that the proximal section completely bunched in the tissue tract, with the delivery device completely withdrawn.

FIG. 7A through 7F depicts the mechanism that controls the delivery sheath to deliver the device in the vessel and tissue tract. The device embodied in FIG. 1 is used as an example of how the mechanism would operate for any of the embodiments of the invention. FIG. 7A shows the delivery sheath locking into the introducer sheath with the distal end of the delivery sheath. FIG. 7B depicts the mechanism which provides both tension on the tension members and motion with the plunger using the movement of the block to push the plunger into the delivery sheath that is locked into the introducer sheath with a control arm at the proximal end of the delivery sheath for simultaneously applying tension on the tension member or members. FIG. 7C depicts the delivery sheath sliding into the introducer sheath. FIG. 7D depicts the delivery sheath locked into the introducer sheath and extending into the introducer sheath and beyond the distal end of it into the interior of the vessel. The distal section of the closure device extends beyond the distal end of the delivery sheath in a "T" formation in preparation for placing the distal section of the closure device at the interior of the vessel wall. The device also depicts a control arm for controlling the tension member or members and plunger. FIG. 7E depicts the delivery sheath extending through the introducer sheath with the delivery sheath and introducer sheath extended into the interior of the vessel, with the distal end of the delivery sheath extending beyond the introducer sheath, and the distal section of the closure device protruding from the distal end of the delivery sheath in a "T" formation in preparation for placing the distal section of the closure device at the interior wall of the vessel. FIG. 7F depicts a cross-sectional view of the delivery mechanism for delivering the device.

FIG. 8A-8C depicts the mechanism for placing and the deploying the closure device.

DETAILED DESCRIPTION OF THE INVENTION

Figures 3A, 3B:
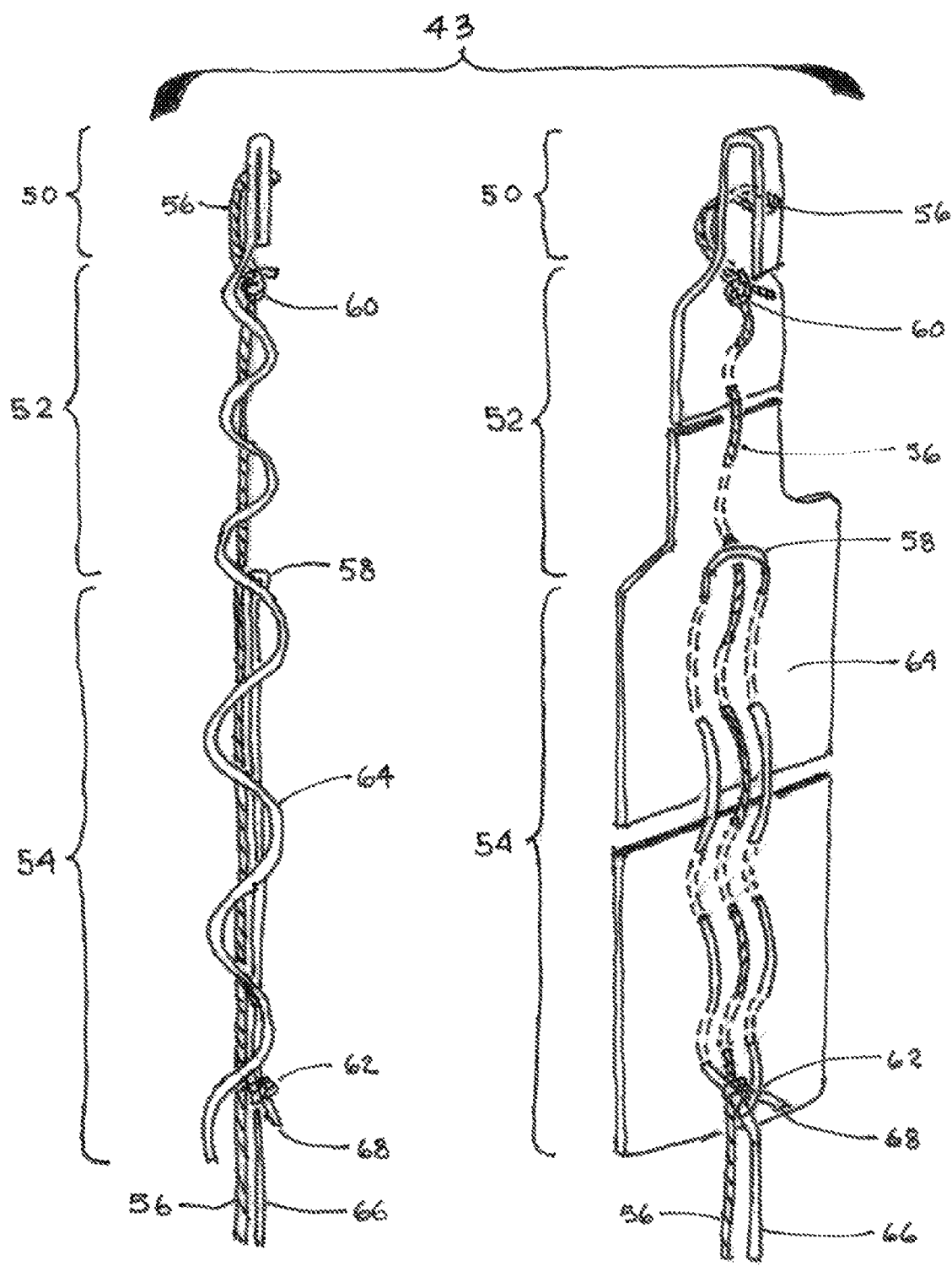
FIG. 3A is a side view of an embodiment of the device having a distal section, a middle section, and a proximal section. This particular embodiment has two tension members, one in the distal section, and running also through the middle and proximal sections, and a second tension member through the proximal section.
FIG. 3B is a flat view of the same embodiment as in FIG. 3A, having a slip knot in the second tension member at the proximal end, and an end knot in the first tension member at the distal section.

The closure device is made of a bunchable material that bunches within the tissue tract. The device is delivered in a delivery sheath through the introducer sheath through the tissue tract to a vessel having a puncture hole. The distal end of the device is seated against the vessel wall and material comprising the proximal section of the device is bunched within the tissue tract to provide an environment for blood coagulation, closure of the puncture hole and sealing the space within the tissue tract. The material of the device is a biocompatible material and can be partly or fully bioabsorbable or biodegradable.

Turning now to the figures, FIG. 1A-1F depict the general embodiment of a device 17 having a distal section, a proximal section and a single tension member running through both the distal section and proximal sections and controlled by proximal ends that are proximal to the proximal section. That being said, FIG. 1A depicts a side view of an embodiment of device 17 having a distal section 2 and a proximal section 4. The distal section 2 has a tension member 8 that loops through both the distal section 2 and the proximal section 4, weaving in and out of the bunchable material 6, and having a first proximal end 10 and a second proximal end 12 and a slip knot 14 that is tied by first proximal end 10 around second proximal end 12. FIG. 1B is a flatter view of the same device 17 as depicted in FIG. 1A, having the tension member 8 that loops around in the distal section 2 and through the proximal section 4, with a first proximal end 10 and a second proximal end 12 resulting in ends 10 and 12 at the proximal section 4. Slip knot 14 is made using first proximal end 10 around second proximal end 12.

FIG. 1C is a slightly different embodiment of 17 from FIGS. 1A and 1B in that end knot 15 is used in the proximal section 4 with first proximal end 10 instead of a slip knot. Tension member 8 is looped through both the distal section 2 and the proximal section 4, and also results in second proximal end 12. Pulling on second proximal end 12 bunches the bunchable material 6. FIG. 1D presents yet another embodiment of device 17 providing a looped knot 16 using proximal end 10, and leaving free and dangling second proximal end 12. In any of these embodiments the knots may be looped knots or end knots, provided they hold the tension member at the position of the knot in the material where the tension member is attached by a knot.

FIG. 1E depicts an embodiment of the device 17 where a single tension member 22 is run through both the distal section 2 and the proximal section 4, having an anchor knot 20 in the distal section, and a proximal end 18 at the proximal section. FIG. 1F depicts a slight variation on this embodiment depicting a looped knot anchor 24 in the distal section 2, with tension member 22 running also through proximal section 4.

FIG. 2A through 2F depict another several embodiments in a device 31 that have some elements in common, that is having a distal section and proximal section, and a first and second tension member. Accordingly, turning to FIGS. 2A and 2B there is depicted a side view of device 31 in FIG. 2A and a flat view in FIG. 2B of a device 31 having a distal section 2 and a proximal section 4, and a bunchable material 6 comprising the proximal section 4. First tension member 26 in distal section 2 ends in slip knot 40. First tension member 26 extends also through proximal section. Proximal end 30 of second tension member 28 extends from proximal section 4 through bunchable material 6, forming slip knot 34 around other proximal end 32.

FIGS. 2C and 2D depict an embodiment of device 31 having an anchor knot 36 in second tension member 28 having proximal ends 30 and 32 resulting from proximal section 4. Distal section 2 has first tension member 26 and slip knot 40. FIG. 2D illustrates a looped anchor knot 16 with end 30 instead of the straight anchor knot 36 of FIG. 2C. Ends 32 and 26 emerge at the proximal end in FIG. 2D as with FIG. 2C. Having first and second tension members allows the practitioner to first position the distal section 2 and then to bunch the proximal section 4 in the tissue tract.

FIGS. 2E and 2F depict an embodiment of device 31 also having the two tension members, a first tension member 26 in distal section 2 and a second tension member 28 in proximal section 4. FIG. 2E depicts an anchor knot 20 in first tension member 26 in distal section 2, and FIG. 2F depicts a looped anchor knot 24 in first tension member 26 in distal section 2. Both FIGS. 2E and 2F depict first tension member resolving in the proximal section 4, and both FIGS. 2E and 2F also depicts second tension member 28 resolving in first and second proximal ends 30 and 32 in proximal section 4. Slip knot 34 secures and controls second tension member 30 around second proximal end 32.

FIGS. 3A and 3B depict side view and flat view respectively of an embodiment of device 43 having a distal section 50, a middle section 52 and a proximal section 54. Distal section 50 has first tension member 56 having slip knot 60. First tension member 56 also weaves through middle section 52 and proximal section 54 to resolve at the proximal most part of proximal section 54. Second tension member 58 begins at proximal section 54 and loops around to finish proximally in ends 68 and 66, end 68 forming a slip knot 62 around end 66. Proximal section 54 and middle section 52 are made of bunchable material 64 as depicted in the side view of device 43 in FIG. 3A.

FIGS. 4A, 4B and 4C depict an embodiment of the device 17 having a distal section 84, proximal section 86 and tension member 96 in a vessel 82, through a vessel opening 70, and within a tissue tract 80. The delivery sheath 72 fits within the introducer sheath 78 within the tissue tract 80. The distal section 84 is placed up against the interior wall of the vessel 82. Tension member 90 is looped through distal section 84 and proximal section 86, and resolves in ends 94 and 96, with slip knot 92 actuated by plunger 88 moving toward the distal section against delivery sheath wall 76. FIG. 4B depicts device 17 having the distal section 84 placed in the vessel 82 and having the proximal section 86 bunched by pushing on the plunger 88 along plunger wall 76 within delivery sheath 72 which is within introducer sheath 78 to move the slip knot 92 towards the distal section 84 and bunching the material of the proximal section 86 through the contraction of tension member loop 90 having proximal ends 94 and 96. While the plunger 88 is moving distally, tension is being placed on end 96 of tension member loop 90 which causes the slip knot 92 to slide and the loop of tension member 90 to tighten. FIG. 4C depicts device 17 fully deployed in the tissue tract 80 having distal section 84 placed in vessel 82, and proximal section 86 completely bunched in tissue tract 80, having slip knot 92 pushed tightly against proximal section 86 and having short end 94 and longer end 96 resting in tissue tract 80. The delivery sheath 72 and introducer sheath 78 of device 17 of FIG. 4B are removed and blood is allowed to flow through vessel 82 without leaking from opening 70 (opening 70 depicted in FIG. 4A).

FIGS. 5A, 5B and 5C depicts the embodiment of the device 31 having a distal section, a proximal section and first and second tension members. FIG. 5A depicts distal section 2 placed within the opening 70 and seated in vessel 82. First tension member 26 holds distal section 2 in place using slip knot 40. Proximal section 4 made of bunchable material begins to bunch in device 31 in FIG. 5A using ends 30 and 32, the end 30 forming slip knot 34. Plunger 88 of delivery sheath 72 is placed within the introducer sheath 78, all placed within tissue tract 80. As the device 31 gets deployed in FIG. 5B slip knot 34 tightens over end 32 using end 30, pushed by pusher 88 against delivery sheath wall 76 through delivery sheath 72, within introducer sheath 78 in tissue tract 80. As a result of the bunching of proximal section 4, first tension member 26 and second tension member 28 are pulled tightly through proximal section 4 as pusher 88 moves up through delivery sheath 72 against delivery sheath wall 76. FIG. 5C depicts the fully deployed device 31 having distal section 2 placed flatly in vessel 82 and proximal section 4 bunched tightly up against slip knot 40, having slip knot 34 pushed tightly against proximal section 4, with ends 30, 32 and 26 remaining in the tissue tract after removal of the delivery sheath and introducer sheath.

Figure 6A:
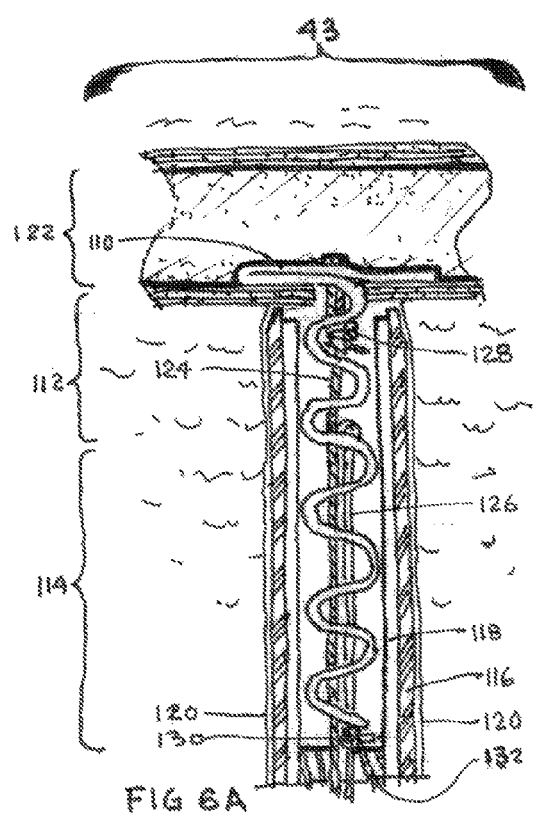
FIGS. 6A, 6B, 6C, and 6D depicts the embodiment of FIGS. 3A and 3B in the context of a vessel and tissue tract.
Figure 6B:
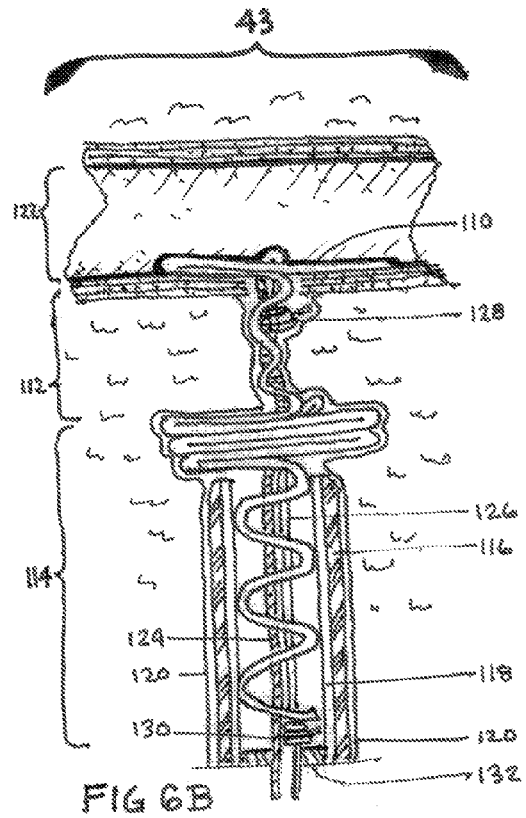
Figure 6C:
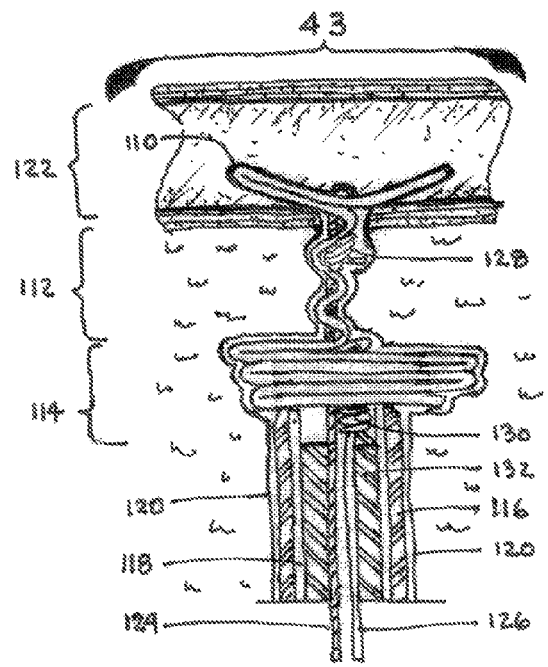
Figure 6D:
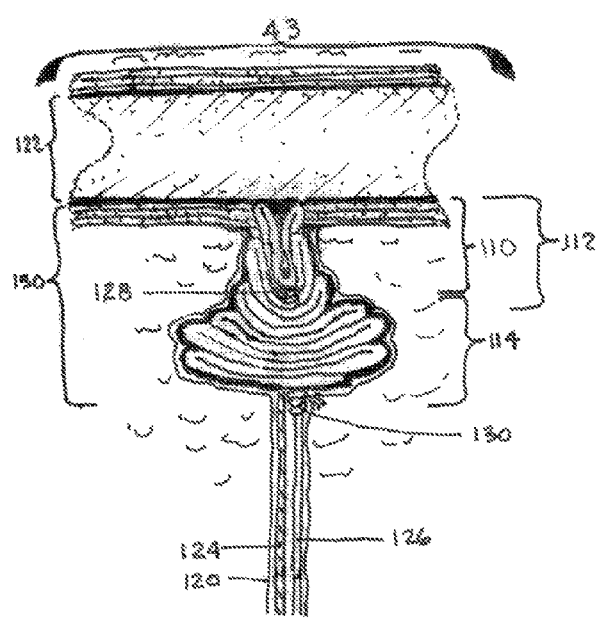

FIGS. 6A, 6B, 6C and 6D depict device 43 having a distal section 110, a middle section 112, and a proximal section 114 with a first tension member 124, and a second tension member 126. FIG. 6A depicts delivery sheath 118 within introducer sheath 116 within tissue tract 120 with plunger 132 in delivery sheath 118, all positioned for actuation and release of device 43. In FIG. 6A distal section 110 of device 43 is already placed in vessel 122. Slip knot 128 is tied over first tension member 124. Middle section 112 acts as a spacer to keep the proximal section a measured distance from the outside of the vessel wall while the proximal section 114 is being bunched. The measured distance is maintained for the purpose of later withdrawing the distal section 110 from the vessel into the tissue tract adjacent to the middle section. The proximal section 114 bunches over second tension member 126 with some tightening coming from slip knot 130 around second tension member 126. FIG. 6B depicts device 43 having a middle section 112 in tissue tract 120 with slip knot 128 pushed tightly against distal section 110. Proximal section 114 is beginning to bunch in tissue tract 120, as introducer sheath 116 and delivery sheath 118 are being withdrawn from tissue tract 120 to release the bunchable material of proximal section 114 over first tension member 124 and second tension member 126. FIG. 6C depicts full activation of plunger 132 through delivery sheath 118 within introducer sheath 116 in tissue tract 120 with slip knot 130 pushed tightly up against fully released and bunched proximal section 114 in tissue tract 120 with first tension member 124 fully pulled against slip knot 128, and second tension member 126 is fully pulled against slip knot 130. Also in FIG. 6C, distal section 110 is beginning to fold in on itself in vessel 122, as tension is applied to first tension member 124 for a second time. FIG. 6D depicts device 43 fully released and positioned in tissue tract 120 (with delivery sheath 118 and introducer sheath 116 removed), having distal section 110 fully folded in on itself and withdrawn from vessel 122 so that distal section 110 is no longer in vessel 122, but rather outside it in the early portion of tissue tract 120, adjacent to the now bunched middle section 112. Middle section 112 is compressed around distal section 110 in FIG. 6D, and proximal section 114 is fully bunched against slip knot 130 which is pulled along second tension member 126. First tension member 124 is pulled tightly against slip knot 128.

FIG. 7A depicts the mechanism of delivery device 55, having delivery sheath 160, introducer sheath 168 locking member 162, plunger guide block 170, and side port 172. The delivery sheath 160 fits inside introducer sheath 168, and inside the delivery sheath resides the slidable plunger 132. The side port 172 provides access for flushing and other coordinate procedures to facilitate the process. Locking members 162 allow the introducer sheath 168 to lock into place while plunger 132 is still available to slide forward and back as needed for deployment of the device. The distal portion of the introducer sheath 164 defines the interface where the delivery sheath slides through the introducer sheath to deliver the device.

FIG. 7B shows the distal portion 164 of introducer sheath 168, and the delivery sheath 160 locked within introducer sheath 168. FIG. 7B also depicts the tension member anchor 166 around which one or more tension members 96 can be strung and pulled, or otherwise controlled through the center of plunger 132.

FIG. 7C depicts the particular sliding and locking mechanism between delivery sheath 160 and introducer sheath 168 at plunger guide block 170. Side port 172 is unaffected by the locking mechanism.

FIG. 7D shows further locking member 162 having introducer sheath 168 locked around delivery sheath 160. Proximal end of plunger 132 is also shown, as is the tension member anchor 166 and proximal end of the tension member 96. Delivery sheath 160 is shown in vessel 174 having distal section 175 of the device released from the delivery sheath 160 and rotated 90 degrees for eventual positioning at the wall of vessel 174.

FIG. 7E depicts a closer view of the action depicted in FIG. 7D inside the vessel 174, where the delivery sheath 160 is within introducer sheath 168 within vessel 174, delivery sheath 160 having distal section 175 released into vessel 174 and rotated 90 degrees for eventual placement at the opening in vessel wall 174.

FIG. 7F depicts a side cross-sectional view of the delivery device and mechanism. Working back from the tip of the partially delivered device 175, there is the tension member 96 that slips inside plunger 132, which slides within delivery sheath 160, which is within introducer sheath 168, from which side port 172 can be located for peripheral delivery of fluids and such, resolving in a substantial proximal end of introducer sheath 168, within which slides a middle portion of delivery sheath 160, and the introducer sheath 168 can lock into locking member 162 at certain points in the delivery process. Plunger 132 continues to extend beyond plunger guide block 170 which serves to slide plunger forward and back stably as needed. Tension member 96 extends beyond the plunger and is wrapped around fulcrum 171, and further controlled and placed into tension by wrapping around tension member anchor 166. Thus, it can be seen how several slidable members (notably the plunger 132, delivery sheath 160, and introducer sheath 168) control the placement of the distal end 175 of the device and using tension on the tension member 96 with the fulcrum 171 and tension anchor member 166, deploy the device inside the vessel wall and tissue tract.

FIG. 8A-8C depict the same mechanism as detailed in FIG. 7A-7F, but with the addition of an actual movable handle 204 and some of its coordinate parts to facilitate the activities necessary to deliver the device. In the embodiment of FIG. 8A, the mechanism is open and the plunger drive block 198 feeds forward and backward the plunger 132. Plunger guide block 170 serves to guide the plunger 132 into the delivery (160) and introducer (168) sheaths when the introducer sheath 168 is locked at locking members 162. Introducer sheath 168 still contains delivery sheath 160 and plunger 132, and external to the skin puncture, side port 172. Guide plate 200 holds and stabilizes fulcrum 171, plunger drive block 198 and plunger guide block 170. The plunger 132 passes through the plunger guide block 170 and plunger drive block 198. Handle 204 and scissor arm 202 rotate over pivot 206 which moves the plunger drive block 198 either closer or further away from the fulcrum 171 (depending on whether the handle 204 is opening or closing), making the tension member 96 taught upon "closing" the handle 204; FIG. 8B depicts partial closure of the mechanism to thus create pressure on tension member 96 and move plunger 132 distally by closing handles 204. FIG. 8C depicts a further closure from the intermediate closure depicted in FIG. 8B. Handle 204 is squeezed together and pivot 206 further pulls in scissor arm 202 which places the maximal pressure on tension member 96, which tension in coordination with pushing of the plunger 132, allows the device to leave the delivery sheath and become deployed.

The bunchable material for the device is biocompatible and can also be a biodegradable material, and will preferably biodegrade within some reasonable period of time after placement at the puncture hole, roughly equal to the healing time for the wound at the puncture hole and in the tissue tract. The material is in a form amendable to bunching and also amenable to intercalating with the tissue, cells and proteins of the environment at the puncture wound and in the tissue tract. The form of the material can include, for example, a weave or braid, or natural or synthetic polymer matrix, or any material that can bunch. The braid may be such that when placed in tension, stretches and thins and when placed under compression, shortens and expands. One form of the device is one which folds upon itself thus increasing its surface area per unit length.

The bunchable material of the device including any of any the sections of the device can be made of any bunchable materials or malleable materials, some biodegradable and some not, for example polyglycolitic acid (PGA), polyglycolitic lactic acid (PGLA), polylactic acid (PLA), Polydioxanone, Polycaprolactone, Polyhydroxybutyrate, silk, nylon, collagen, extracellular matrix, polytetrafluoroethylene (PTFE), expanded polytetrafluoroethylene (EPTFE), Dacron, a metal, a metal alloy, a plastic, an elastic material, a polymer, an inert material, a fused segment of material, a melted segment of material, a fabric, a braid, a weave, and a generally bunchable material. Similar materials to these may be used having the ability to provide bunchable layers that cause interference to a blood flow and promote coagulation by blocking any blood flow out of the puncture wound into the tissue tract. Also the bunching of material promotes healing and wound closure in the tissue tract. The material can be a single material or combination of one or more materials. A natural polymer matrix can include an extracellular matrix, such as derived from mammalian tissue including liver basement membrane, urinary bladder submucosa, small intestine submucosa and stomach submucosa, which are known in the art. The matrix can also be a synthetic collagen-type or other matrix, of which many are known in the art. Sheet form of extracellular matrix can be cut to the proper shape and formed in folding sheets with perforations for folding, and can also be threaded with a tension member as described in other embodiments. The extracellular matrix should be made malleable and bunchable rather than rigid and stiff, which may be possible if the material is soaked in a softening solution that encourages the material to bunch without cracking and breaking.

The distal sections of these devices have a stiffened rod or stick of material at the distal most end, with maybe one bunched section after that before the device retreats into the tissue tract. The rod or stick can be made by fusing the material of the device at the distal most end. The distal section will be turned in the delivery sheath to penetrate the vessel opening. After penetrating the vessel opening, the distal section is rotated 90 degrees to seat against the vessel wall. Turning now to the illustrations of FIG. 4, distal section 84 of the device 17 in FIGS. 4A, 4B and 4C enters the puncture hole 70 as a point or tip and the plunger 88 pushes the distal section 84 out into the vessel lumen 82 while simultaneously tension is applied to the tension member end 96 causing the tip of the distal section 84 to rotate 90 degrees. Delivery sheath 72 and introducer sheath 78 are withdrawn from the vessel until distal section 84 seats firmly against vessel wall. Plunger 88 pushes up on proximal section 86 to encourage bunching of the material in tissue tract 80 using also tension that can be created on tension member 96 having slip knot 92. As plunger 88 pushes distally, proximal section 86 becomes completely folded and delivery sheath 72 and introducer sheath 78 can be removed leaving fully deployed device 17 to block puncture hole 70 and tissue tract 88

Embodiment 31 in FIGS. 5A, 5B and 5C has a tension member in distal section 2 and a tension member in proximal section 4. Separate tension members provide for control of the distal section 2 first while placing it against the vessel wall of vessel 82. Secondly, control of the proximal section 4 is facilitated by pulling on the second tension member 28 and sliding slip knot 34 over end 32 to cause bunching of proximal section 4 in tissue tract 80. Eventually the bunching is complete and the tissue tract 80 is sealed and the delivery sheath 72 and introducer sheath 78 can be removed from tissue tract 80. Ends 26 and 32 will remain in the tissue tract also with short end 30 and slip knot 34.

Embodiment 43 in FIGS. 6A, 6B, 6C and 6D is depicted being deployed in vessel 122 and tissue tract 120. Embodiment 43 has a middle section 112. The middle section can be the same width as the proximal section 114 or it can be narrower. The advantage of a narrower middle section is that the middle section will disrupt the puncture hole less. The middle section does not necessarily bunch but it can. Generally it acts as a connector between the distal and proximal sections. Although the first tension member 124 from the distal section 110 runs through the middle section 112, the middle section 112 is bunched (if at all) essentially from the retraction of distal section 110 as shown in FIG. 6D. The bunching of proximal section 114 occurs with the second tension member 126 pulling up with the pressure from slip knot 130 along the second tension member 126. Plunger 132 pushes the proximal section 114 up through the delivery sheath. After the proximal section 114 has bunched as tightly as possible a second pull on the first tension member 124 receives a new pull to retreat the distal section 110 out of the vessel 122 and into the very first part of the tissue tract 120 next to the middle section. This way a smooth unoccluded vessel 122 remains. Eventually the delivery sheath 118 and introducer sheath 116 are removed so that the device can degrade in the tissue tract as the tissue tract heals.

Operation of mechanism 55 depicted in FIGS. 7A, 7B, 7C, 7D, 7E, and 7F details a tension member anchor 166 that can control the first or second tension member as well as applying motion to the plunger 132. The delivery sheath 160 of device 55 locks into the introducer sheath 168 at position 162. The delivery sheath 160 extends distal of the introducer sheath 168 so that the distal section 175 can be placed in the vessel and otherwise manipulated to deploy the device.

Preferably, the bunchable material will bioabsorb or biodegrade as the wound heals so that months after the procedure and after the healing process is completed, there will be no evidence, or virtually no evidence of the material having been in the body. The proximal section can have demarcations to encourage bunching of the section as the tension member is pulled. These demarcations can be perforation, or weakened lines, or supported lines that encourage bunching as a tension member is pulled. The demarcations along the material of the proximal section can be equally spaced or unequally spaced. Thus, the bunching areas of the section, depending on the spacing of the demarcations, can be roughly equal, or may be in fact unequal. The structural benefits provided by the folded proximal section in the tissue tract include creating an environment in the tract for the wound to heal and any blood seeping from the puncture hole to coagulate.

The tension member is made of a biocompatible material, and can be a biodegradable material, provided that such material has enough initial tensile strength to do the work required of the tension member in pulling through the proximal section and bunching the material in the proximal section in the tissue tract. Tension members attached to the distal section also need to control the rotation and seating of the distal section and in the embodiments where the distal section is retracted from the vessel to also be able to accomplish that task. Thus, the tension member material can be PGLA, PGA, PLA, polydioxanone, polycaprolactone, polyhydroxybutyrate, suture, silk, Dacron or propylene, or similar materials capable of holding and conveying a tensile strength when the tension member is pulled to bunch or otherwise control the device. The tension member may also be any of the materials listed in other sections, provided the material can do the work that the tension member needs to do. The tension member material needs also to be relatively smooth so that upon pulling of the material to cause it to bunch the tension member will be able to slide through the material and draw it together in the tissue tract.

The method of wound closure of the invention involves providing the closure device and delivering it to the puncture wound and bunching it within the tissue tract. Typically the tissue tract will be accessed with a delivery sheath that contains an unbunched, fully extended version of the closure device. The distal section of the device having a distal most rod-like fused section of material is placed through the puncture hole and seated on the inside wall of the accessed vessel. Typically, the distal section will be in its narrowest configuration in order to go through the puncture hole and then by manipulation of the tension member and plunger during deployment of the distal section in the vessel, will be turned or rotated about 90 degrees to seat against the vessel wall inside the blood vessel. The proximal section of the device is deployed by a combination of pushing the plunger distally while the delivery sheath stays in the same place and pulling on the tension member to effect a bunching of the material of the proximal section as the material leaves the delivery sheath. The introducer sheath is always equal with or proximal of the tip of the delivery sheath as both are being withdrawn progressively from the tissue tract. Generally, the deployment of the proximal section includes using a plunger in the delivery sheath that pushes the proximal section distally, and counters the pulling pressure from the tension member. After the proximal section is bunched in the tissue tract, the tension members are released from the control mechanism allowing the delivery sheath and introducer sheath to be further withdrawn after which the excess length of the tension members can be clipped at the surface of the skin. The tension members also act as safety tethers, maintaining attachment to the closure device in the event that it is improperly deployed and has to be withdrawn and repositioned in the tissue tract, or removed and replaced with a new device. The bunching of the proximal section is designed to provide structural impediment to bleeding in the tissue tract and to provide an environment for the wound to heal.

The method of the invention that uses the embodiment depicted in FIG. 6 indicates the following steps: placing the closure device having a distal, middle and proximal section into a delivery sheath and placing the delivery sheath into an introducer sheath in the tissue tract. From this position, the delivery sheath is directed to the interior opening of the vessel or cavity. The plunger in the delivery mechanism and delivery sheath is pushed within the delivery sheath distally enough to deploy the distal section into the vessel. The distal section is then rotated about 90 degrees inside the vessel or cavity while pulling the first tension member at the same time that the plunger is pushed. This dual action provides the control to place the rotated distal section against the interior or the vessel or cavity by then pulling back on the delivery sheath until said rotated distal section seats against the vessel wall. The introducer sheath and delivery sheath are gradually withdrawn along the tissue tract while pushing of the plunger lodged within the delivery sheath distally to release the middle and proximal sections in the tissue tract. The bunching of the proximal section is accomplished by pulling the second tension member (while pushing the plunger). Once the proximal section is deployed from the delivery sheath and fully bunched the puncture wound is closed. Finally, in this embodiment, the first tension member is pulled a second time to fold and withdraw the distal section from the vessel into the tissue tract so that it rests near the middle section, outside of the vessel. In this way the vessel can resume full fluid flow without the distal section lodged at the vessel wall.

The invention includes methods of placing, deploying, positioning, and adjusting the devices, for the purpose of closing puncture wounds in a patient. The methods may be practiced using any sequence of necessary steps possible in order to accomplish placing the device in the patient for closing the puncture wound. The steps may be practiced in a specific order or in any order deemed practical by the practitioner conducting the procedure.

The mechanism that controls deployment of the device from the delivery sheath provides both tension on the tension members and motion with the plunger using the movement of the block to push the plunger into the delivery sheath that is locked into the introducer sheath with a control arm at the proximal end of the delivery sheath for approximately simultaneously applying tension on the tension member or members.

The invention is a closure device for closing a puncture wound, said device deliverable in a delivery sheath, said puncture wound having a length along a tissue tract that resolves in an interior opening of a vessel or cavity, said closure device comprising:

(a) a distal section for placing inside said interior opening of said vessel or cavity, said distal section lodged in a delivery sheath having proximal and distal ends, said delivery sheath capable of penetrating said wound along said length of said wound to pass through said interior opening and release said distal section, said released distal section capable of rotation of about 90 degrees to provide resistance against said interior opening, (b) a proximal section connected to said distal section, said proximal section comprising a bunchable material capable of bunching in said tissue tract upon deployment, said proximal section released from said delivery sheath in an unbunched state, bunchable upon release, (c) a tension member connected from said distal section through said proximal section for rotating said distal section 90 degrees in said interior opening inside said vessel or cavity, and for bunching said proximal section, upon release of said proximal section in said tissue tract, thereby closing said puncture wound with said distal section rotated 90 degrees inside said vessel or cavity and said proximal section bunched in said tissue tract and (d) a plunger lodged within said delivery sheath for rotating said distal section 90 degrees in coordination with said tension member by pushing said plunger towards said distal section and pulling said tension member against the pushing of said plunger, thereby closing said puncture wound with said distal section rotated 90 degrees inside said vessel or cavity and said proximal section bunched in said tissue tract.

The closure device can further comprise that said plunger is also capable of bunching said proximal section after rotation of said distal section by pushing distally with said plunger while said tension member is pulled proximally.

The closure device can further comprise a plunger for bunching said proximal section by pushing distally with said plunger while said tension member is pulled proximally.

The closure device contemplates wherein said tension member is looped through said distal section and proximal section using a single tension member having first and second proximal ends. An embodiment also contemplates wherein said tension member passes through said distal section and said proximal section once and is knotted at said distal section, said tension member having a single end proximal to said proximal section. Said looped tension member can be attached to itself by a slip knot of a first end of the tension member around a second end of the tension member. The looped tension member can be fixed by one knot in a first end of the tension member.

The distal and proximal sections can comprise a material selected from the group consisting of polyglycolytic acid (PGA), PGLA, PLA, polydioxanone, polycaprolactone, polyhydroxybutyrate, collagen, a polymer matrix, extracellular matrix, silk, Dacron, PTFE, EPTFE, a bioabsorbable material, a biodegradable material, a biocompatible material, a metal, a metal alloy, a plastic, an elastic material, a polymer, an inert material, a fused segment of material, a melted segment of material, a fabric, a braid, a weave, and a foldable material.

The tension member can comprise a material selected from the group consisting of polyglycolytic acid (PGA), PGLA, PLA, polydioxanone, polycaprolactone, polyhydroxybutyrate, collagen, a polymer matrix, extracellular matrix, silk, Dacron, suture, a bioabsorbable material, a biodegradable material, a biocompatible material, a metal, a metal alloy, a plastic, an elastic material, a polymer, an inert material, a thread, and a strand.

The invention is also a closure device for closing a puncture wound, said device deliverable in a delivery sheath, said puncture wound having a length along a tissue tract that resolves in an interior opening of a vessel or cavity, said closure device comprising:

(a) a distal section for placing inside said interior opening of said vessel or cavity, said distal section lodged in a delivery sheath having proximal and distal ends, said delivery sheath capable of penetrating said wound along said length of said wound to pass through said interior opening and release said distal section, said released distal section capable of rotation of about 90 degrees to provide resistance against said interior opening, (b) a proximal section connected to said distal section, said proximal section comprising a bunchable material capable of bunching in said tissue tract upon deployment, said proximal section also released from said delivery sheath in an unbunched state, bunchable upon release, (c) a first tension member connected to said distal section for rotating said distal section 90 degrees inside said vessel or cavity and placing said distal section inside said interior opening of said vessel or cavity to provide resistance against said interior opening, (d) a second tension member connected to said proximal section for bunching said bunchable material of said proximal section within said tissue tract, thereby closing said puncture wound, and (e) a plunger for pushing said distal section into said vessel and rotating it 90 degrees in coordination with a pulling of said first tension member, and for bunching said proximal section by pushing distally with said plunger while said second tension member is pulled proximally.

The first tension member can be looped through said distal section and comprises a slip knot formed of a first and second end of the first tension member.

The second tension member can be looped through said proximal section and comprises a slip knot formed of a first and second end of the second tension member.

The distal, and proximal sections can comprise a material selected from the group consisting of polyglycolytic acid (PGA), PGLA, PLA, polydioxanone, polycaprolactone, polyhydroxybutyrate, collagen, a polymer matrix, extracellular matrix, silk, Dacron, PTFE, EPTFE, a bioabsorbable material, a biodegradable material, a biocompatible material, a metal, a metal alloy, a plastic, an elastic material, a polymer, an inert material, a fused segment of material, a melted segment of material, a fabric, a braid, a weave, and a foldable material.

The first and second tension members can comprise a material selected from the group consisting of polyglycolytic acid (PGA), PGLA, PLA, polydioxanone, polycaprolactone, polyhydroxybutyrate, collagen, a polymer matrix, extracellular matrix, silk, Dacron, suture, a bioabsorbable material, a biodegradable material, a biocompatible material, a metal, a metal alloy, a plastic, an elastic material, a polymer, an inert material, a thread, and a strand.

The invention is also a closure device for closing a puncture wound, said device deliverable in a delivery sheath, said puncture wound having a length along a tissue tract that resolves in an interior opening of a vessel or cavity, said closure device comprising:

(a) a distal section for placing inside said interior opening of said vessel or cavity, said distal section lodged in a delivery sheath having proximal and distal ends, said delivery sheath capable of penetrating said wound along said length of said wound to pass through said interior opening and release said distal section, said released distal section capable of rotation of about 90 degrees to provide resistance against said interior opening, (b) a middle section connected to said distal section so that upon rotation of said distal section, said middle section exterior to said vessel or cavity, remaining in connection with said distal section, (c) a proximal section connected to said middle section, said proximal section comprising a bunchable material capable of bunching in said tissue tract upon deployment, said proximal section also released from said delivery sheath in an unbunched state, bunchable upon release, (d) a first tension member connected to said distal section for rotating said distal section 90 degrees inside said vessel or cavity and placing said distal section inside said interior opening of said vessel or cavity to provide resistance against said interior opening, (e) a second tension member connected to said proximal section for bunching said bunchable material of said proximal section within said tissue tract, thereby closing said puncture wound, and (f) a plunger for pushing said distal section into said vessel and rotating it 90 degrees in coordination with a pulling of said first tension member, and for bunching said proximal section by pushing distally with said plunger while said second tension member is pulled proximally.

The first tension member is looped through said distal section and comprises a slip knot formed from a first and second end of the first tension member. The second tension member is looped through said proximal section and comprises a slip knot formed from a first and second end of the second tension member.

The middle section can be narrower than said distal section so as to provide minimal disturbance between said interior opening of said vessel or cavity and said tissue tract.

The distal, middle and proximal sections can comprise a material selected from the group consisting of polyglycolytic acid (PGA), PGLA, PLA, polydioxanone, polycaprolactone, polyhydroxybutyrate, collagen, a polymer matrix, extracellular matrix, silk, Dacron, PTFE, EPTFE, a bioabsorbable material, a biodegradable material, a biocompatible material, a metal, a metal alloy, a plastic, an elastic material, a polymer, an inert material, a fused segment of material, a melted segment of material, a fabric, a braid, a weave, and a foldable material.

The first and second tension members can comprise a material selected from the group consisting of polyglycolytic acid (PGA), PGLA, PLA, polydioxanone, polycaprolactone, polyhydroxybutyrate, collagen, a polymer matrix, extracellular matrix, silk, Dacron, suture, a bioabsorbable material, a biodegradable material, a biocompatible material, a metal, a metal alloy, a plastic, an elastic material, a polymer, an inert material, a thread, and a strand.

The invention is also a closure device for closing a puncture wound, said device deliverable in a delivery sheath, said puncture wound having a length along a tissue tract that resolves in an interior opening of a vessel or cavity, said closure device comprising:

(a) a distal section for placing inside said interior opening of said vessel or cavity, said distal section lodged within a delivery sheath having proximal and distal ends, said delivery sheath capable of penetrating said wound along said length of said wound to pass through said interior opening and release said distal section, said released distal section capable of rotation of about 90 degrees to provide resistance against said interior opening, (b) a middle section connected to said distal section so that upon rotation of said distal section, said middle section exterior to said vessel or cavity, remaining in connection with said distal section, (c) a proximal section connected to said middle section, said proximal section comprising a bunchable material capable of bunching in said tissue tract upon deployment, said proximal section also released from said delivery sheath in an unbunched state, bunchable upon release, (d) a first tension member connected to said distal section for rotating said distal section 90 degrees inside said vessel or cavity and placing said distal section inside said interior opening of said vessel or cavity to provide resistance against said interior opening, and (e) a second tension member connected to said proximal section for bunching said bunchable material of said proximal section within said tissue tract, thereby closing said puncture wound, (f) a plunger for pushing said distal section into said vessel and rotating it 90 degrees in coordination with a pulling of said first tension member, and for bunching said proximal section by pushing distally with said plunger while said second tension member is pulled proximally, (g) said first tension member capable of withdrawing said distal section from inside said vessel or cavity to be next to and folded into said middle section within said tissue tract, thereby removing said distal section from said vessel or cavity.

The middle section can be narrower than said distal section so as to provide minimal disturbance between said interior opening of said vessel or cavity and said tissue tract.

The first tension member can be looped through said distal section, and resolve in two ends forming a slip knot.

The second tension member can be looped through said proximal section and resolves in a first end and a second end forming a slip knot for pulling said second tension member to bunch said proximal section.

The devices of the invention can optionally include a plunger for bunching the proximal section while a tension member that runs through the proximal section is pulled tight, either with an end knot or a slip knot configuration of the tension member.

The distal, middle and proximal sections can comprise a material selected from the group consisting of polyglycolytic acid (PGA), PGLA, PLA, polydioxanone, polycaprolactone, polyhydroxybutyrate, collagen, a polymer matrix, extracellular matrix, silk, Dacron, PTFE, EPTFE, a bioabsorbable material, a biodegradable material, a biocompatible material, a metal, a metal alloy, a plastic, an elastic material, a polymer, an inert material, a fused segment of material, a melted segment of material, a fabric, a braid, a weave, and a foldable material.

The first and second tension members comprises a material selected from the group consisting of polyglycolytic acid (PGA), PGLA, PLA, polydioxanone, polycaprolactone, polyhydroxybutyrate, collagen, a polymer matrix, extracellular matrix, silk, Dacron, suture, a bioabsorbable material, a biodegradable material, a biocompatible material, a metal, a metal alloy, a plastic, an elastic material, a polymer, an inert material, a thread, and a strand.

The invention is also a closure device for closing a puncture wound, said device deliverable in a delivery sheath, said puncture wound having a length along a tissue tract that resolves in an interior opening of a vessel having fluid flow, said closure device comprising:

a short stiff front section capable of rotation 90 degrees upon deployment from said delivery sheath and upon pushing of a plunger also lodged in said delivery sheath capable of placement inside said vessel for seating said device in said vessel, said short front section having a first tension member and said short front section connected to a long bunchable back section that bunches upon deployment from said delivery sheath using said plunger to push it out from said delivery sheath in a plunging action and a second tension member running through the bunchable section to pull against said seated front section in opposition to said plunging action to release said long back section from said delivery sheath and to bunch it in said tissue tract.

The invention includes a method of closing a puncture wound, said wound having a length along a tissue tract that resolves in an interior opening of a vessel or cavity comprising:

placing the closure device for closing a puncture wound into a delivery sheath and placing said delivery sheath into an introducer sheath in said tissue tract, and directing said delivery sheath to said interior opening of said vessel or cavity, said device deliverable in a delivery sheath, said puncture wound having a length along a tissue tract that resolves in an interior opening of a vessel or cavity, said closure device comprising:

(a) a distal section for placing inside said interior opening of said vessel or cavity, said distal section lodged in a delivery sheath having proximal and distal ends, said delivery sheath capable of penetrating said wound along said length of said wound to pass through said interior opening and release said distal section, said released distal section capable of rotation of about 90 degrees to provide resistance against said interior opening, (b) a proximal section connected to said distal section, said proximal section comprising a bunchable material capable of bunching in said tissue tract upon deployment, said proximal section released from said delivery sheath in an unbunched state, bunchable upon release, and (c) a tension member connected from said distal section through said proximal section for rotating said distal section 90 degrees in said interior opening inside said vessel or cavity, and for bunching said proximal section, upon release of said proximal section in said tissue tract, thereby closing said puncture wound with said distal section rotated 90 degrees inside said vessel or cavity and said proximal section bunched in said tissue tract, and (d) a plunger lodged within said delivery sheath for rotating said distal section 90 degrees in coordination with said tension member by pushing said plunger towards said distal section and pulling said tension member against the pushing of said plunger, thereby closing said puncture wound with said distal section rotated 90 degrees inside said vessel or cavity and said proximal section bunched in said tissue tract, pushing said plunger positioned within said delivery sheath distally enough to deploy said distal section in said vessel, rotating said distal section about 90 degrees inside said vessel or cavity while pulling said tension member and pushing said plunger distally towards the puncture hole in the vessel, placing said rotated distal section against said interior of said vessel or cavity by pulling back on said delivery sheath, pulling on said tension member, and pushing on said plunger until said rotated distal section seats against the vessel wall, withdrawing said introducer sheath and delivery sheath gradually along said tissue tract, pushing said plunger lodged within said delivery sheath distally to release said proximal section in said tissue tract, and bunching said proximal section by pulling said tension member and pushing said plunger, thereby providing closure for said puncture wound in said vessel and along said tissue tract.

The invention also includes a method of closing a puncture wound, said wound having a length along a tissue tract that resolves in an interior opening of a vessel or cavity comprising:

placing a closure device for closing a puncture wound into a delivery sheath and placing said delivery sheath into an introducer sheath in said tissue tract, and directing said delivery sheath to said interior opening of said vessel or cavity, said device deliverable in a delivery sheath, said puncture wound having a length along a tissue tract that resolves in an interior opening of a vessel or cavity, said closure device comprising:

(a) a distal section for placing inside said interior opening of said vessel or cavity, said distal section lodged in a delivery sheath having proximal and distal ends, said delivery sheath capable of penetrating said wound along said length of said wound to pass through said interior opening and release said distal section, said released distal section capable of rotation of about 90 degrees to provide resistance against said interior opening, (b) a proximal section connected to said distal section, said proximal section comprising a bunchable material capable of bunching in said tissue tract upon deployment, said proximal section also released from said delivery sheath in an unbunched state, bunchable upon release, (c) a first tension member connected to said distal section for rotating said distal section 90 degrees inside said vessel or cavity and placing said distal section inside said interior opening of said vessel or cavity to provide resistance against said interior opening, and (d) a second tension member connected to said proximal section for bunching said bunchable material of said proximal section within said tissue tract, thereby closing said puncture wound, and (e) a plunger lodged within said delivery sheath for rotating said distal section 90 degrees in coordination with said first tension member by pushing said plunger towards said distal section and pulling said first tension member against the pushing of said plunger, thereby closing said puncture wound with said distal section rotated 90 degrees inside said vessel or cavity and said proximal section bunched in said tissue tract, pushing said plunger positioned within said delivery sheath distally enough to deploy said distal section in said vessel, rotating said distal section about 90 degrees inside said vessel or cavity while pulling said first tension member and pushing said plunger distally towards the puncture hole in the vessel, placing said rotated distal section against said interior of said vessel or cavity by pulling back on said delivery sheath, pulling on said first tension member, and pushing on said plunger until said rotated distal section seats against the vessel wall, withdrawing said introducer sheath and delivery sheath gradually along said tissue tract, pushing said plunger lodged within said delivery sheath distally to release said proximal section in said tissue tract, and bunching said proximal section by pulling said second tension member and pushing said plunger, thereby providing closure for said puncture wound in said vessel and along said tissue tract.

The invention is also a method of closing a puncture wound, said wound having a length along a tissue tract that resolves in an interior opening of a vessel or cavity comprising:

placing a closure device for closing a puncture wound, said device deliverable in a delivery sheath, said puncture wound having a length along a tissue tract that resolves in an interior opening of a vessel or cavity into a delivery sheath and placing said delivery sheath into an introducer sheath in said tissue tract, and directing said delivery sheath to said interior opening of said vessel or cavity, said closure device comprising:

(a) a distal section for placing inside said interior opening of said vessel or cavity, said distal section lodged in a delivery sheath having proximal and distal ends, said delivery sheath capable of penetrating said wound along said length of said wound to pass through said interior opening and release said distal section, said released distal section capable of rotation of about 90 degrees to provide resistance against said interior opening, (b) a middle section connected to said distal section so that upon rotation of said distal section, said middle section exterior to said vessel or cavity, remaining in connection with said distal section, (c) a proximal section connected to said middle section, said proximal section comprising a bunchable material capable of bunching in said tissue tract upon deployment, said proximal section also released from said delivery sheath in an unbunched state, bunchable upon release, (d) a first tension member connected to said distal section for rotating said distal section 90 degrees inside said vessel or cavity and placing said distal section inside said interior opening of said vessel or cavity in coordination with pushing on a plunger towards the puncture hole in the vessel to provide resistance against said interior opening, and (e) a second tension member connected to said proximal section for bunching said bunchable material of said proximal section within said tissue tract, thereby closing said puncture wound.

(f) a plunger lodged within said delivery sheath for rotating said distal section 90 degrees in coordination with said first tension member by pushing said plunger towards said distal section and pulling said first tension member against the pushing of said plunger, thereby closing said puncture wound with said distal section rotated 90 degrees inside said vessel or cavity and said proximal section bunched in said tissue tract, pushing a plunger positioned within said delivery sheath distally enough to deploy said distal section in said vessel rotating said distal section about 90 degrees inside said vessel or cavity while pulling a first tension member and pushing said plunger distally toward the puncture hole in the vessel, placing said rotated distal section against said interior of said vessel or cavity by pulling back on the delivery sheath until said rotated distal section seats against the vessel wall, withdrawing said introducer sheath and delivery sheath gradually along said tissue tract pushing said plunger lodged within said delivery sheath distally to release said middle and proximal sections in said tissue tract, and bunching said proximal section in said tissue tract by pulling said second tension member, thereby providing closure for said puncture wound.

The invention also includes a method of closing a puncture wound, said wound having a length along a tissue tract that resolves in an interior opening of a vessel or cavity comprising:

placing a closure device for closing a puncture wound, into a delivery sheath and placing said delivery sheath into an introducer sheath in said tissue tract, and directing said delivery sheath to said interior opening of said vessel or cavity, said device deliverable in a delivery sheath, said puncture wound having a length along a tissue tract that resolves in an interior opening of a vessel or cavity, said closure device comprising:

(a) a distal section for placing inside said interior opening of said vessel or cavity, said distal section lodged within a delivery sheath having proximal and distal ends, said delivery sheath capable of penetrating said wound along said length of said wound to pass through said interior opening and release said distal section, said released distal section capable of rotation of about 90 degrees to provide resistance against said interior opening, (b) a middle section connected to said distal section so that upon rotation of said distal section, said middle section exterior to said vessel or cavity, remaining in connection with said distal section, (c) a proximal section connected to said middle section, said proximal section comprising a bunchable material capable of bunching in said tissue tract upon deployment, said proximal section also released from said delivery sheath in an unbunched state, bunchable upon release, (d) a first tension member connected to said distal section for rotating said distal section 90 degrees inside said vessel or cavity by pulling on said first tension member and pushing on said plunger and placing said distal section inside said interior opening of said vessel or cavity to provide resistance against said interior opening, and (e) a second tension member connected to said proximal section for bunching said bunchable material of said proximal section within said tissue tract, thereby closing said puncture wound, (f) a plunger lodged within said delivery sheath for rotating said distal section 90 degrees in coordination with said first tension member by pushing said plunger towards said distal section and pulling said first tension member against the pushing of said plunger, thereby closing said puncture wound with said distal section rotated 90 degrees inside said vessel or cavity and said proximal section bunched in said tissue tract, (g) said first tension member capable of withdrawing said distal section from inside said vessel or cavity to be next to and folded into said middle section within said tissue tract, thereby removing said distal section from said vessel or cavity.

pushing a plunger positioned within said delivery sheath distally enough to deploy said distal section in said vessel rotating said distal section about 90 degrees inside said vessel or cavity while pulling said first tension member, and placing said rotated distal section against said interior of said vessel or cavity by pulling back on the delivery sheath, pulling on said first tension member, and pushing on said plunger towards the puncture hole in the vessel until said rotated distal section seats against the vessel wall, withdrawing said introducer sheath and delivery sheath gradually along said tissue tract pushing said plunger lodged within said delivery sheath distally toward said puncture hole in said vessel to release said middle and proximal sections in said tissue tract, bunching said proximal section by pulling said second tension member and pushing on said plunger towards said vessel hole, thereby providing closure for said puncture wound, and pulling said first tension member a second time to withdraw said distal section from said vessel into said tissue tract in close proximity with said middle section.

A kit can be assembled including a bunching closure device by itself or the bunching closure device loaded in a delivery sheath. Directions for use of the folding device and delivery sheath and for delivery and deployment of the device are included. The kit is housed in a container, and a description of the materials that make up the device can be included.

Also, it is contemplated that any optional feature of the inventive variations described may be set forth and claimed independently, or in combination with any one or more of the features described herein. Reference to a singular item, includes the possibility that there are a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

All references cited are incorporated in their entirety. Although the foregoing invention has been described in detail for purposes of clarity of understanding, it will be obvious that certain modifications may be practiced within the scope of the appended claims.

What is claimed is:

1. A closure device for closing a puncture wound, said device deliverable in a delivery sheath, said puncture wound having a length along a tissue tract that resolves in an interior opening of a vessel or cavity, said closure device comprising:
   (a) a distal section for placing inside said interior opening of said vessel or cavity, said distal section lodged in a delivery sheath having proximal and distal ends, said delivery sheath capable of penetrating said wound along said length of said wound to pass through said interior opening and release said distal section, said released distal section capable of rotation of about 90 degrees to provide resistance against said interior opening,
   (b) a middle section connected to said distal section so that upon rotation of said distal section, said middle section exterior to said vessel or cavity, remaining in connection with said distal section,
   (c) a proximal section connected to said middle section, said proximal section comprising a bunchable material capable of bunching in said tissue tract upon deployment, said proximal section also released from said delivery sheath in an unbunched state, bunchable upon release,
   (d) a first tension member connected to said distal section for rotating said distal section 90 degrees inside said vessel or cavity and placing said distal section inside said interior opening of said vessel or cavity to provide resistance against said interior opening, and
   (e) a second tension member connected to said proximal section for bunching said bunchable material of said proximal section within said tissue tract, thereby closing said puncture wound, and
   (f) a plunger lodged within said delivery sheath for rotating said distal section 90 degrees in coordination with said first tension member by pushing said plunger towards said distal section and pulling said first tension member against the pushing of said plunger,
   thereby closing said puncture wound with said distal section rotated 90 degrees inside said vessel or cavity and said proximal section bunched in said tissue tract.

2. The closure device of claim 1, further comprising that said plunger is also capable of bunching said proximal section after rotation of said distal section by pushing distally with said plunger while said second tension member is pulled proximally.

3. The closure device of claim 1, wherein said first tension member is looped through said distal section and said second tension member is looped through said proximal section each using a single tension member having first and second proximal ends.

4. The closure device of claim 2, wherein said first tension member is looped through said distal section and said second tension member is looped through said proximal section each using a single tension member having first and second proximal ends.

5. The closure device of claim 1, wherein said first tension member passes through said distal section and said second tension member passes through said proximal section once and is knotted at an end closest to the puncture hole in the vessel, said tension members each having a single end proximal to said proximal section and close to said skin surface.

6. The closure device of claim 2, wherein said first tension member passes through said distal section once and is knotted at an end closest to the puncture hole and said second tension member passes through said proximal section once and is knotted at an end closest to the puncture hole in the vessel, said tension members each having a single end proximal to said proximal section and close to said skin surface.

7. The closure device of claim 3, wherein said looped second tension member is attached to itself by a slip knot of a first end around a second end, said slip knot being close to the skin surface.

8. The closure device of claim 4, wherein said looped second tension member is attached to itself by a slip knot of a first end of the tension member around a second end of the tension member.

9. The closure device of claim 2, wherein said looped first tension member is fixed by one knot in a first end of the first tension member.

10. The closure device of claim 2, wherein said looped second tension member is fixed by one knot in a first end of the second tension member.

11. The closure device of claim 4, wherein said looped second tension member is fixed by one knot in a first end of the second tension member.

12. The closure device of claim 1, wherein said distal and proximal sections comprise a material selected from the group consisting of polyglycolytic acid (PGA), PGLA, PLA, polydioxanone, polycaprolactone, polyhydroxybutyrate, collagen, a polymer matrix, extracellular matrix, silk, Dacron, PTFE, EPTFE, a bioabsorbable material, a biodegradable material, a biocompatible material, a metal, a metal alloy, a plastic, an elastic material, a polymer, an inert material, a fused segment of material, a melted segment of material, a fabric, a braid, a weave, and a foldable material.

13. The closure device of claim 1, wherein said tension member comprises a material selected from the group consisting of polyglycolytic acid (PGA), PGLA, PLA, polydioxanone, polycaprolactone, polyhydroxybutyrate, collagen, a polymer matrix, extracellular matrix, silk, Dacron, suture, a bioabsorbable material, a biodegradable material, a biocompatible material, a metal, a metal alloy, a plastic, an elastic material, a polymer, an inert material, a thread, and a strand.

14. A closure device for closing a puncture wound, said device deliverable in a delivery sheath, said puncture wound having a length along a tissue tract that resolves in an interior opening of a vessel having fluid flow, said closure device comprising:
   a short stiff front section capable of rotation 90 degrees upon deployment from said delivery sheath and upon pushing of a plunger also lodged in said delivery sheath capable of placement inside said vessel for seating said device in said vessel, said short front section having a first tension member and said short front section connected to
   a middle section so that upon rotation of said distal section, said middle section resides exterior to said vessel or cavity, remaining in connection with said distal section,
   a long bunchable back section connected to said middle section that bunches upon deployment from said delivery sheath using a plunger to push it out from said delivery sheath in a plunging action and a second tension member running through the bunchable section to pull against said seated front section in opposition to said plunging action to release said long back section from said delivery sheath and to bunch it in said tissue tract.

15. The device of claim 14, wherein said distal and proximal sections comprise a material selected from the group consisting of polyglycolytic acid (PGA), PGLA, PLA, polydioxanone, polycaprolactone, polyhydroxybutyrate, collagen, a polymer matrix, extracellular matrix, silk, Dacron, PTFE, EPTFE, a bioabsorbable material, a biodegradable material, a biocompatible material, a metal, a metal alloy, a plastic, an elastic material, a polymer, an inert material, a fused segment of material, a melted segment of material, a fabric, a braid, a weave, and a foldable material.

16. The closure device of claim 14, wherein said tension member comprises a material selected from the group consisting of polyglycolytic acid (PGA), PGLA, PLA, polydioxanone, polycaprolactone, polyhydroxybutyrate, collagen, a polymer matrix, extracellular matrix, silk, Dacron, suture, a bioabsorbable material, a biodegradable material, a biocompatible material, a metal, a metal alloy, a plastic, an elastic material, a polymer, an inert material, a thread, and a strand.

17. The device of claim 14, wherein said second tension member is looped through said proximal section and having first and second proximal ends residing close to the skin surface.

18. The device of claim 17, wherein said looped tension member is attached to itself by a slip knot of a first end of the tension member around a second end of the tension member.

19. The device of claim 14, wherein said second tension member passes through said proximal section once and is knotted close to the puncture hole in the vessel, said tension member having a single end proximal to said proximal section and close to said skin surface.

20. The device of claim 14, wherein said second tension member is fixed by one knot in a first end of the tension member close to said puncture hole in the vessel.

* * * * *